(12) United States Patent
Watanabe

(10) Patent No.: US 6,514,984 B1
(45) Date of Patent: Feb. 4, 2003

(54) TREATMENT FOR ALZHEIMER'S DISEASE

(75) Inventor: August Masaru Watanabe, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/529,565

(22) Filed: Apr. 12, 2000

Related U.S. Application Data

(60) Provisional application No. 60/066,035, filed on Nov. 14, 1997.

(51) Int. Cl.$^7$ .................. A61K 31/403; A61K 31/437; A61K 31/4375; A61K 31/519

(52) U.S. Cl. ................ 514/293; 514/411; 514/224.5; 514/229.8; 514/250; 514/347; 544/31; 544/95; 544/101; 544/250; 544/346; 546/87; 548/428; 548/430; 548/432; 548/441; 548/448

(58) Field of Search ........................... 546/87; 548/428, 548/430, 432, 441, 448; 514/293, 411

(56) References Cited

U.S. PATENT DOCUMENTS

| | | | | |
|---|---|---|---|---|
| 4,837,240 A | * | 6/1989 | Thielke et al. | 514/294 |
| 4,968,699 A | * | 11/1990 | Hoeltje et al. | 514/235.5 |
| 5,478,857 A | * | 12/1995 | Clemens et al. | 514/381 |
| 5,563,164 A | * | 10/1996 | Clemens et al. | 514/381 |
| 5,650,426 A | * | 7/1997 | Borrett et al. | 514/411 |
| 5,654,326 A | * | 8/1997 | Bach et al. | 514/419 |
| 5,756,501 A | * | 5/1998 | Sabb | 514/248 |
| 5,830,911 A | * | 11/1998 | Failli et al. | 514/411 |
| 6,037,361 A | * | 3/2000 | Roth et al. | 514/411 |
| 6,057,340 A | * | 5/2000 | Kelly et al. | 514/326 |
| 6,214,879 B1 | * | 4/2001 | Abraham et al. | 514/579 |
| 6,219,514 B1 | * | 9/2001 | Illig et al. | 514/447 |

FOREIGN PATENT DOCUMENTS

| | | |
|---|---|---|
| WO | WO99/25339 | 5/1999 |

\* cited by examiner

Primary Examiner—Richard L. Raymond
(74) Attorney, Agent, or Firm—Roger S. Benjamin

(57) ABSTRACT

A method is disclosed for the prevention and treatment of Alzheimer's disease by administering to a human in need thereof an effective amount of a substituted tricyclic sPLA$_2$ inhibitor.

9 Claims, No Drawings

TREATMENT FOR ALZHEIMER'S DISEASE

This application claims the benefit of Provisional Application No. 60/066,035, filed Nov. 14, 1997.

BACKGROUND OF THE INVENTION

Alzheimer's disease is a degenerative disorder of the human brain. Clinically, it appears as a progressive dementia. Its histopathology is characterized by degeneration of neurons, gliosis, and the abnormal deposition of proteins in the brain. Pathological hallmarks include neurofibrillary tangles (paired helical filaments) and amyloid deposits within the parenchyma and cerebral vasculature.

Recent studies indicate that a major component of the pathology of Alzheimer's disease is chronic inflammation. See, J. Schnabel, Science, 260:1719–1720 (1993).

Administration of nonsteroidal anti-inflammatory drugs appears to slow the advance of Alzheimer's disease. Understanding this inflammatory component of Alzheimer's disease may lead to advances in methods of treating patients suffering from this disease.

The structure and physical properties of human non-pancreatic secretory phospholipase $A_2$ (hereinafter called, "$sPLA_2$") has been described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; The Journal of Biological Chemistry, Vol. 264, No. 10, Issue of Apr. 5, 1989; pp. 5335–5338, and "Structure and Properties of a Human Nonpancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; The Journal of Biological Chemistry, Vol. 264, No. 10, Issue of Apr. 5, 1989; pp. 5768–5775, the disclosures of which are incorporated herein by reference.

It is believed that $sPLA_2$ is a rate limiting enzyme in the arachidonic acid cascade which hydrolyzes membrane phospholipids.

The scientific literature suggests NSAIDs may be beneficial in the treatment of Alzheimer's Disease. Moreover, COX-2 inhibitors are currently being tested for treatment of Alzheimer's.

$PLA_2$ inhibitors have been proposed as treatment for Alzheimer's disease (see, U.S. Pat. Nos. 5,478,857 and 5,563,164), but typically these have been cytosolic phospholipase $A_2$ inhibitors.

Because of the debilitating effects of Alzheimer's disease there continues to exist a need for effective treatments. This invention provides methods for the treatment of Alzheimer's disease in mammals.

SUMMARY OF THE INVENTION

This invention is a method of treating a mammal, including a human, susceptible to having Alzheimer's disease, to prevent or delay the onset of Alzheimer's disease; said method comprising administering to said mammal a prophylactically effective amount of substituted tricyclic $sPLA_2$ inhibitor or a pharmaceutically acceptable salt, solvate or prodrug derivative thereof.

This invention is also a method of treating a mammal, including a human, already afflicted with Alzheimer's disease to prevent or diminish the rate of further deterioration; said method comprising administering to said mammal a therapeutically effective amount substituted tricyclic $sPLA_2$ inhibitor compound or a pharmaceutically acceptable salt, solvate or prodrug derivative thereof.

DETAILED DESCRIPTION AND PREFERRED EMBODIMENTS

All temperatures stated herein are in degrees Celsius (° C.). All units of measurement employed herein are in weight units except for liquids which are in volume units.

General Definitions

The term "prophylactically effective amount" is the quantity of substituted tricyclic $sPLA_2$ inhibitor required to prevent or significantly delay the onset of Alzheimer's disease in a mammal susceptible (by reason of age, family history, etc.) to contracting Alzheimer's disease.

The term "therapeutically effective amount" is the quantity of substituted tricyclic $sPLA_2$ inhibitor sufficient to prevent or retard the progress of Alzheimer's disease in a mammal already afflicted with Alzheimer's disease.

The term "parenteral" means not through the alimentary canal but by some other route such as subcutaneous, intramuscular, intraorbital, intracapsular, intraspinal, intrasternal, or intravenous.

The term "active compound" means one or more substituted tricyclic $sPLA_2$ inhibitors used in the method of the invention as further described in Formula III or named below.

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl tert butyl, n-pentyl, isopentyl, neopentyl, heptyl, hexyl, octyl, nonyl, decyl, undecyl, dodecyl, tridecyl, tetradecyl and the like. The term "alkyl" includes —$(C_1-C_2)$alkyl, —$(C_1-C_4)$alkyl, —$(C_1-C_6)$alkyl, —$(C_5-C_{14})$alkyl, and —$(C_1-C_{10})$alkyl.

The term "alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" denotes such radicals as ethynyl, propynyl, butynyl, pentynyl, hexynyl, heptynyl as well as di- and tri-ynes.

The term "halo" means chloro, fluoro, bromo or iodo.

The term "—$(C_1-C_4)$alkoxy", as used herein, denotes a group such as methoxy, ethoxy, n-propoxy, isopropoxy, n-butoxy, t-butoxy and like groups, attached to the remainder of the molecule by the oxygen atom.

The term "phenyl$(C_1-C_4)$alkyl" refers to a straight or branched chain alkyl group having from one to four carbon atoms attached to a phenyl ring which chain is attached to the remainder of the molecule. Typical phenylalkyl groups include benzyl, phenylethyl, phenylpropyl, phenylisopropyl, and phenylbutyl.

The term "—$(C_1-C_4)$alkylthio" defines a straight or branched alkyl chain having one to four carbon atoms attached to the remainder of the molecule by a sulfur atom. Typical —$(C_1-C_4)$alkylthio groups include methylthio, ethylthio, propylthio, butylthio and the like.

The term "—($C_3$–$C_{14}$)cycloalkyl" includes groups such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl and the like. The term "—($C_3$–$C_{14}$)cycloalkyl" includes and —($C_3$–$C_7$)cycloalkyl.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexeyl, acenaphthylenyl, and anthracenyl, biphenyl, bibenzylyl and related bibenzylyl homologues represented by the formula (bb),

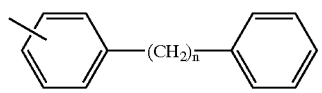
(bb)

where n is an integer from 1 to 8.

The term, "non-interfering substituent", refers to radicals suitable for substitution at positions 1, 2, 3, 7 and/or 8 on the tricyclic nucleus (as depicted in Formula III) and radical(s) suitable for substitution on the heterocyclic radical and carbocyclic radical as defined above. Illustrative non-interfering radicals are hydrogen, —($C_1$–$C_{12}$)alkyl, —($C_2$–$C_6$)alkenyl, —($C_2$–$C_6$)alkynyl, —($C_7$–$C_{12}$)aralkyl, —($C_7$–$C_{12}$)alkaryl, —($C_3$–$C_8$)cycloalkyl, —($C_3$–$C_8$)cycloalkenyl, phenyl, tolulyl, xylenyl, biphenyl, —($C_1$–$C_6$)alkoxy, —($C_2$–$C_6$)alkenyloxy, —($C_2$–$C_6$)alkynyloxy, —($C_1$–$C_{12}$)alkoxyalkyl, —($C_1$–$C_{12}$)alkoxyalkyloxy, —($C_1$–$C_{12}$)alkylcarbonyl, —($C_1$–$C_{12}$)alkylcarbonylamino, —($C_1$–$C_{12}$)alkoxyamino, —($C_1$–$C_{12}$)alkoxyaminocarbonyl, —($C_1$–$C_{12}$)alkylamino, —($C_1$–$C_6$)alkylthio, —($C_1$–$C_{12}$)alkylthiocarbonyl, —($C_1$–$C_6$)alkylsulfinyl, —($C_1$–$C_6$)alkylsulfonyl, —($C_1$–$C_6$)haloalkoxy, —($C_1$–$C_6$)haloalkylsulfonyl, —($C_1$–$C_6$)haloalkyl, —($C_1$–$C_6$)hydroxyalkyl, —$(CH_2)_n CN$, —$(CH_2)_n NR^9 R^{10}$, —$C(O)O$ ($C_1$–$C_6$ alkyl), —$(CH_2)_n O(C_1$–$C_6$ alkyl), benzyloxy, phenoxy, phenylthio, —$(CONHSO_2 R)$, —CHO, amino, amidino, halo, carbamyl, carboxyl, carbalkoxy, —$(CH_2)_n CO_2 H$, cyano, cyanoguanidinyl, guanidino, hydrazide, hydrazino, hydrazido, hydroxy, hydroxyamino, nitro, phosphono, —$SO_3 H$, thioacetal, thiocarbonyl, and ($C_1$–$C_6$) alkylcarbonyl; where n is from 1 to 8 and $R^9$ and $R^{10}$ are independently —($C_1$–$C_4$)alkyl or phenyl($C_1$–$C_4$)alkyl. A preferred group of non-interfering substituents include hydrogen, halo, —($C_1$–$C_3$)alkyl, —($C_3$–$C_4$)cycloalkyl, —($C_3$–$C_4$)cycloalkenyl, —O($C_1$–$C_2$)alkyl or —S($C_1$–$C_2$)alkyl.

The term, "acidic group" means an organic group which when attached to a tricyclic nucleus, through suitable linking atoms (hereinafter defined as the "acid linker"), acts as a proton donor capable of hydrogen bonding. Illustrative of an acidic group are the following:

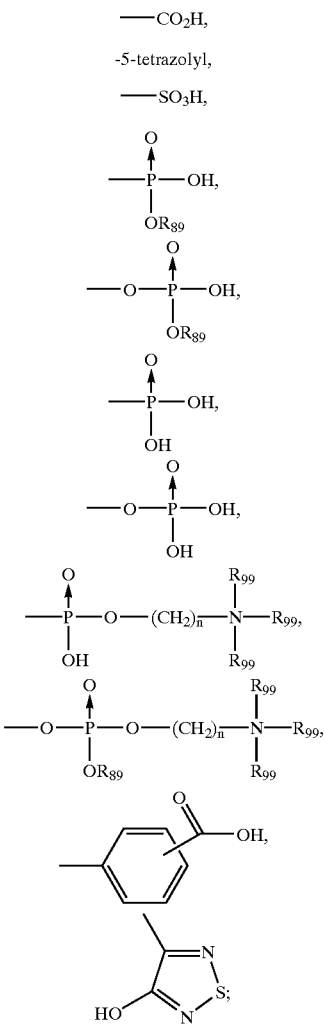

where n is 1 to 8, $R_{89}$ is a metal or —($C_1$–$C_{10}$)alkyl, and $R_{99}$ is hydrogen or —($C_1$–$C_{10}$)alkyl.

The words, "acid linker" refer to a divalent linking group symbolized as, —$(L_a)$—, which has the function of joining the 5 or 6 position of the tricyclic nucleus to an acidic group in the general relationship:

(tricyclic nucleus)-$(L_a)$-Acidic Group

The words, "acid linker length", refer to the number of atoms (excluding hydrogen) in the shortest chain of the linking group —$(L_a)$— that connects the 5 or 6 position of the tricyclic nucleus with the acidic group. The presence of a carbocyclic ring in —$(L_a)$— counts as the number of atoms approximately equivalent to the calculated diameter of the carbocyclic ring. Thus, a benzene or cyclohexane ring in the acid linker counts as 2 atoms in calculating the length of —$(L_a)$—. Illustrative acid linker groups are;

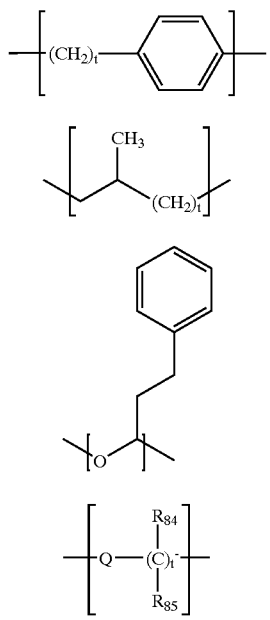

there t is 1 to 5, Q is selected from the group —(CH$_2$)—, —O—, —NH—, and —S—, and R$_{84}$ and R$_{85}$ are each independently selected from hydrogen, —(C$_1$-C$_{10}$)alkyl, aryl, —(C$_1$-C$_{10}$)alkaryl, —(C$_1$-C$_{10}$)aralkyl, carboxy, carbalkoxy, and halo, when t is one (1), groups (a), (b), (c) and (d) have acid linker lengths of 3, 3, 2, and 2, respectively.

The salts of the above tricyclics are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively nontoxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," J. Phar. Sci., 66: 1–19 (1977)).

Compounds of the invention may have chiral centers and exist in optically active forms. R- and S-isomers and racemic mixtures are contemplated by this invention. A particular stereoisomer may be prepared by known methods using stereospecific reactions with starting materials containing asymmetric centers already resolved or, alternatively, by subsequent resolution of mixtures of stereoisomers using known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Other preferred prodrug esters include morpholinoethyloxy and diethylaminocarbonylmethoxy.

I. sPLA$_2$ INHIBITORS USEFUL IN THE METHOD OF THE INVENTION

Carbazole and tetrahydrocarbazole SPLA$_2$ inhibitors and methods of making these compounds are set out in U.S. patent application Ser. No. 09/063066 filed Apr. 21, 1998 (titled, "Substituted Carbazoles and 1,2,3,4-Tetrahydrocarbazoles"), the entire disclosure of which is incorporated herein by reference. The method of the invention includes treatment of a mammal, including a human, with these compounds.

The method of the invention is for treatment of a mammal, including a human, afflicted with Alzheimer's Disease, said method comprising administering to said human a therapeutically effective amount carbazole or tetrahydrocarbazole represented by the following:

A compound of the formula (Ie)

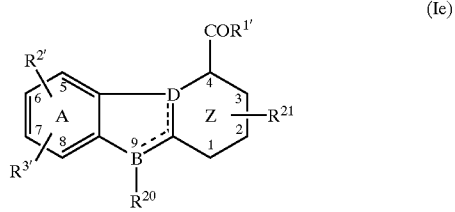

(Ie)

wherein;

A is phenyl or pyridyl wherein the nitrogen is at the 5-, 6-, 7- or 8-position;

one of B or D is nitrogen and the other is carbon;

Z is cyclohexenyl, phenyl, pyridyl, wherein the nitrogen is at the 1-, 2-, or 3-position, or a 6-membered heterocyclic ring having one heteroatom selected from the group consisting of sulfur or oxygen at the 1-, 2- or 3-position, and nitrogen at the 1-, 2-, 3- or 4-position;

=== is a double or single bond;

R$^{20}$ is selected from groups (a), (b) and (c) where;
- (a) is —(C$_5$–C$_{20}$)alkyl, —(C$_5$–C$_{20}$)alkenyl, (C$_5$–C$_{20}$) alkynyl, carbocyclic radicals, or heterocyclic radicals, or
- (b) is a member of (a) substituted with one or more independently selected non-interfering substituents; or
- (c) is the group —(L)—R$^{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) and carbon, hydrogen, and oxygen only; and where R$^{80}$ is a group selected from (a) or (b);

R²¹ is a non-interfering substituent;
R1' is —NHNH$_2$, —NH$_2$ or —CONH$_2$;
R2' is selected from the group consisting of —OH, and —O(CH$_2$)$_t$R5' where
R$^{5'}$ is H, —CN, —NH$_2$, —CONH$_2$, —CONR$^9$R$^{10}$— NHSO$_2$R$^{15}$; —CONHSO$_2$R$^{15}$, where R$^{15}$ is —(C$_1$–C$_6$)alkyl or —CF$_3$; phenyl or phenyl substituted with —CO$_2$H or —CO$_2$(C$_1$–C$_4$)alkyl; and —(L$_a$)-(acidic group), wherein —(L$_a$)— is an acid linker having an acid linker length of 1 to 7 and t is 1–5;
R$^{3'}$ is selected from non-interfering substituent, carbocyclic radicals, carbocyclic radicals substituted with non-interfering substituents, heterocyclic radicals, and heterocyclic radicals substituted with non-interfering substituents; or a pharmaceutically acceptable racemate, solvate, tautomer, optical isomer, prodrug derivative or salt thereof;
provided that; when R$^{3'}$ is H, R$^{20}$ is benzyl and m is 1 or 2; R$^{2'}$ cannot be —O(CH$_2$)$_m$H; and
provided that when D is nitrogen, the heteroatom of Z is selected from the group consisting of sulfur or oxygen at the 1-, 2- or 3-position and nitrogen at the 1-, 2-, 3- or 4-position.

Preferred in the practice of the method of the invention are compounds represented by the formula (IIe):

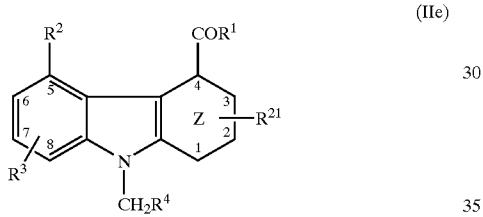

(IIe)

wherein;
Z is cyclohexenyl, or phenyl;
R$^{21}$ is a non-interfering substituent;
R$^1$ is —NHNH$_2$ or —NH$_2$;
R$^2$ is selected from the group consisting of —OH and —O(CH$_2$)$_m$R$^5$ where
R$^5$ is H, —CO$_2$H, —CONH$_2$, —CO$_2$(C$_1$–C$_4$ alkyl);

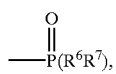

where R$^6$ and R$^7$ are each independently —OH or —O(C$_1$–C$_4$)alkyl; —SO$_3$H, —SO$_3$(C$_1$–C$_4$ alkyl), tetrazolyl, —CN, —NH$_2$, —NHSO$_2$R$^{15}$; —CONHSO$_2$R$^{15}$, where R$^{15}$ is —(C$_1$–C$_6$)alkyl or —CF$_3$, phenyl or phenyl substituted with —CO$_2$H or —CO$_2$(C$_1$–C$_4$)alkyl where m is 1–3;
R$^3$ is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo, or —CF$_3$; —CH$_2$OSi(C$_1$–C$_6$) alkyl, furyl, thiophenyl, —(C$_1$–C$_6$)hydroxyalkyl; or —(CH$_2$)$_n$R$^8$ where R$^8$ is H, —CONH$_2$, —NR$^9$R$^{10}$, —CN or phenyl where R$^9$ and R$^{10}$ are independently —(C$_1$–C$_4$)alkyl or -phenyl(C$_1$–C$_4$)alkyl and n is 1 to 8;
R$^4$ is H, —(C$_5$–C$_{14}$)alkyl, —(C$_3$–C$_{14}$)cycloalkyl, pyridyl, phenyl or phenyl substituted with —(C$_1$–C$_6$)alkyl, halo, —CF$_3$, —OCF$_3$, —(C$_1$–C$_4$)alkoxy, —CN, —(C$_1$–C$_4$)alkylthio, phenyl(C$_1$–C$_4$)alkyl, —(C$_1$–C$_4$) alkylphenyl, phenyl, phenoxy or naphthyl;

or a pharmaceutically acceptable racemate, solvate, tautomer, optical isomer, prodrug derivative or salt, thereof.

Preferred specific compounds including all salts and prodrug derivatives thereof, for practicing the method of the invention are as follows:

9-benzyl-5,7-dimethoxy-1,2,3,4-tetrahydrocarbazole-4-carboxylic acid hydrazide;

9-benzyl-5,7-dimethoxy-1,2,3,4-tetrahydrocarbazole-4-carboxamide;

[9-benzyl-4-carbamoyl-7-methoxy-1,2,3,4-tetrahydrocarbazol-5-yl]oxyacetic acid sodium salt;

[9-benzyl-4-carbamoyl-7-methoxycarbazol-5-yl]oxyacetic acid;

methyl[9-benzyl-4-carbamoyl-7-methoxycarbazol-5-yl]oxyacetic acid;

9-benzyl-7-methoxy-5-cyanomethyloxy-1,2,3,4-tetrahydrocarbazole-4-carboxamide;

9-benzyl-7-methoxy-5-(1H-tetrazol-5-yl-methyl)oxy)-1,2,3,4-tetrahydrocarbazole-4-carboxamide;

{9-[(phenyl)methyl]-5-carbamoyl-2-methyl-carbazol-4-yl}oxyacetic acid;

{9-[(3-fluorophenyl)methyl]-5-carbamoyl-2-methyl-carbazol-4-yl}oxyacetic acid;

{9-[(3-methylphenyl)methyl]-5-carbamoyl-2-methylcarbazol-4-yl}oxyacetic acid;

{9-[(phenyl)methyl]-5-carbamoyl-2-(4-trifluoromethylphenyl)-carbazol-4-yl}oxyacetic acid;

9-benzyl-5-(2-methanesulfonamido)ethyloxy-7-methoxy-1,2,3,4-tetrahydrocarbazole-4-carboxamide;

9-benzyl-4-(2-methanesulfonamido)ethyloxy-2-methoxycarbazole-5-carboxamide;

9-benzyl-4-(2-trifluoromethanesulfonamido)ethyloxy-2-methoxycarbazole-5-carboxamide;

9-benzyl-5-methanesulfonamidoylmethyloxy-7-methoxy-1,2,3,4-tetrahydrocarbazole-4-carboxamide;

9-benzyl-4-methanesulfonamidoylmethyloxy-carbazole-5-carboxamide;

[5-carbamoyl-2-pentyl-9-(phenylmethyl)carbazol-4-yl]oxyacetic acid;

[5-carbamoyl-2-(1-methylethyl)-9-(phenylmethyl)carbazol-4-yl]oxyacetic acid;

[5-carbamoyl-9-(phenylmethyl)-2-[(tri(-1-methylethyl)silyl)oxymethyl]carbazol-4-yl]oxyacetic acid;

[5-carbamoyl-2-phenyl-9-(phenylmethyl)carbazol-4-yl]oxyacetic acid;

[5-carbamoyl-2-(4-chlorophenyl)-9-(phenylmethyl)carbazol-4-yl]oxyacetic acid;

[5-carbamoyl-2-(2-furyl)-9-(phenylmethyl)carbazol-4-yl]oxyacetic acid;

[5-carbamoyl-9-(phenylmethyl)-2-[(tri(-1-methylethyl)silyl)oxymethyl]carbazol-4-yl]oxyacetic acid, lithium salt;

{9-[(phenyl)methyl]-5-carbamoylcarbazol-4-yl}oxyacetic acid;

{9-[(3-fluorophenyl)methyl]-5-carbamoylcarbazol-4-yl}oxyacetic acid;

{9-[(3-phenoxyphenyl)methyl]-5-carbamoylcarbazol-4-yl}oxyacetic acid;

{9-[(2-Fluorophenyl)methyl]-5-carbamoylcarbazol-4-yl}oxyacetic acid;

{9-[(2-trifluoromethylphenyl)methyl]-5-carbamoylcarbazol-4-yl}oxyacetic acid;

{9-[(2-benzylphenyl)methyl]-5-carbamoylcarbazol-4-yl}oxyacetic acid;
{9-[(3-trifluoromethylphenyl)methyl]-5-carbamoylcarbazol-4-yl}oxyacetic acid;
{9-[(1-naphthyl)methyl]-5-carbamoylcarbazol-4-yl}oxyacetic acid;
{9-[(2-cyanophenyl)methyl]-5-carbamoylcarbazol-4-yl}oxyacetic acid;
{9-[(3-cyanophenyl)methyl]-5-carbamoylcarbazol-4-yl}oxyacetic acid;
{9-[(2-methylphenyl)methyl]-5-carbamoylcarbazol-4-yl}oxyacetic acid;
{9-[(3-methylphenyl)methyl]-5-carbamoylcarbazol-4-yl}oxyacetic acid;
{9-[(3,5-dimethylphenyl)methyl]-5-carbamoylcarbazol-4-yl}oxyacetic acid;
{9-[(3-iodophenyl)methyl]-5-carbamoylcarbazol-4-yl}oxyacetic acid;
{9-[(2-Chlorophenyl)methyl]-5-carbamoylcarbazol-4-yl}oxyacetic acid;
{9-[(2,3-difluorophenyl)methyl]-5-carbamoylcarbazol-4-yl}oxyacetic acid;
{9-[(2,6-difluorophenyl)methyl]-5-carbamoylcarbazol-4-yl}oxyacetic acid;
{9-[(2,6-dichlorophenyl)methyl]-5-carbamoylcarbazol-4-yl}oxyacetic acid;
{9-[(3-trifluoromethoxyphenyl)methyl]-5-carbamoylcarbazol-4-yl}oxyacetic acid;
{9-[(2-biphenyl)methyl]-5-carbamoylcarbazol-4-yl}oxyacetic acid;
{9-[(2-Biphenyl)methyl]-5-carbamoylcarbazol-4-yl}oxyacetic acid;
the {9-[(2-Biphenyl)methyl]-5-carbamoylcarbazol-4-yl}oxyacetic acid;
[9-Benzyl-4-carbamoyl-1,2,3,4-tetrahydrocarbaole-5-yl]oxyacetic acid;
{9-[(2-Pyridyl)methyl]-5-carbamoylcarbazol-4-yl}oxyacetic acid;
{9-[(3-Pyridyl)methyl]-5-carbamoylcarbazol-4-yl}oxyacetic acid;
[9-benzyl-4-carbamoyl-8-methyl-1,2,3,4-tetrahydrocarbazol-5-yl]oxyacetic acid;
[9-benzyl-5-carbamoyl-1-methylcarbazol-4-yl]oxyacetic acid;
[9-benzyl-4-carbamoyl-8-fluoro-1,2,3,4-tetrahydrocarbazol-5-yl]oxyacetic acid;
[9-benzyl-5-carbamoyl-1-fluorocarbazol-4-yl]oxyacetic acid;
[9-benzyl-4-carbamoyl-8-chloro-1,2,3,4-tetrahydrocarbazol-5-yl]oxyacetic acid;
[9-benzyl-5-carbamoyl-1-chlorocarbazol-4-yl]oxyacetic acid;
[9-[(Cyclohexyl)methyl]-5-carbamoylcarbazol-4-yl]oxyacetic acid;
[9-[(Cyclopentyl)methyl]-5-carbamoylcarbazol-4-yl]oxyacetic acid;
5-carbamoyl-9-(phenylmethyl)-2-[[(propen-3-yl)oxy]methyl]carbazol-4-yl]oxyacetic acid;
[5-carbamoyl-9-(phenylmethyl)-2[(propyloxy)methyl]carbazol-4-yl]oxyacetic acid; 9-benzyl-7-methoxy-5-((carboxamidomethyl)oxy)-1,2,3,4-tetrahydrocarbazole-4-carboxamide;
9-benzyl-7-methoxy-5-cyanomethyloxy-carbazole-4-carboxamide;
9-benzyl-7-methoxy-5-((1H-tetrazol-5-yl-methyl)oxy)carbazole-4-carboxamide;
9-benzyl-7-methoxy-5-((carboxamidomethyl)oxy)carbazole-4-carboxamide; and
[9-Benzyl-4-carbamoyl-1,2,3,4-tetrahydrocarbaole-5-yl]oxyacetic acid or a pharmaceutically acceptable racemate, solvate, tautomer, optical isomer, prodrug derivative or salt, thereof.

Other desirable carbazole compounds suitable for practicing the method of the invention are selected from those represented by the formula (XXX):

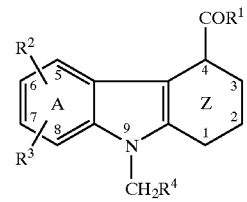

(XXX)

wherein:
$R^1$ is —NHNH$_2$, or —NH$_2$;
$R^2$ is selected from the group consisting of —OH and —O(CH$_2$)$_m$R$^5$ where
$R^5$ is H, —CO$_2$H, —CO$_2$(C$_1$–C$_4$ alkyl);

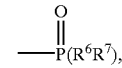

where $R^6$ and $R^7$ are each independently —OH or —O(C$_1$–C$_4$)alkyl; —SO$_3$H, —SO$_3$(C$_1$–C$_4$ alkyl), tetrazolyl, —CN, —NH$_2$, —NHSO$_2$R$^{15}$; —CONHSO$_2$R$^{15}$, where R$^{15}$ is —(C$_1$–C$_6$)alkyl or —CF$_3$, phenyl or phenyl substituted with —CO$_2$H or —CO$_2$(C$_1$–C$_4$)alkyl where m is 1–3;

$R^3$ is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo, or —CF$_3$; —CH$_2$OSi(C$_1$–C$_6$) alkyl, furyl, thiophenyl, —(C$_1$–C$_6$)hydroxyalkyl; or —(CH$_2$)$_n$R$^8$ where R$^8$ is H, —CONH$_2$, —NR$^9$R$^{10}$, —CN or phenyl where R$^9$ and R$^{10}$ are independently —(C$_1$–C$_4$)alkyl or -phenyl(C$_1$–C$_4$)alkyl and n is 1 to 8;

$R^4$ is H, —(C$_5$–C$_{14}$)alkyl, —(C$_3$–C$_{14}$)cycloalkyl, pyridyl, phenyl or phenyl substituted with —(C$_1$–C$_6$)alkyl, halo, —CF$_3$, —OCF$_3$, —(C$_1$–C$_4$)alkoxy, —CN, —(C$_1$–C$_4$)alkylthio, phenyl(C$_1$–C$_4$)alkyl, —(C$_1$–C$_4$) alkylphenyl, phenyl, phenoxy or naphthyl;

A is phenyl or pyridyl wherein the nitrogen is at the 5-, 6-, 7- or 8-position;

Z is cyclohexenyl, phenyl, pyridyl wherein the nitrogen is at the 1-, 2- or 3-position or a 6-membered heterocyclic ring having one heteroatom selected from the group consisting of sulfur or oxygen at the 1-, 2- or 3-position and nitrogen at the 1-, 2-, 3- or 4-position, or wherein one carbon on the heterocyclic ring is optionally substituted with =O;

or a pharmaceutically acceptable racemate, solvate, tautomer, optical isomer, prodrug derivative or salt thereof;

provided that one of A or Z is a heterocyclic ring.

Further desirable specific compounds suitable for the method of the invention are selected from the following:

(R,S)-(9-benzyl-4-carbamoyl-1-oxo-3-thia-1,2,3,4-tetrahydrocarbazol-5-yl)oxyacetic acid; (R,S)-(9-benzyl-4-carbamoyl-1-oxo-3-thia-1,2,3,4-tetrahydrocarbazol-5-yl) oxyacetic acid; [N-benzyl-1-carbamoyl-1-aza-1,2,3,4-tetrahydrocarbazol-8-yl]oxyacetic acid; 4-methoxy-6-methoxycarbonyl-10-phenylmethyl-6,7,8,9-tetrahydropyrido[1,2-a]indole; (4-carboxamido-9-phenylmethyl-4,5-dihydrothiopyrano[3,4-b]indol-5-yl) oxyacetic acid; 3,4-dihydro-4-carboxamidol-5-methoxy-9-phenylmethylpyrano[3,4-b]indole; 2-[(2,9 bis-benzyl-4-carbamoyl-1,2,3,4-tetrahydro-beta-carbolin-5-yl)oxy]acetic acid or a pharmaceutically acceptable racemate, solvate, tautomer, optical isomer, prodrug derivative or salt thereof.

Particularly preferred compounds for the treatment of Alzheimer's Disease are represented by the formulae (Xe) and (XIe) below:

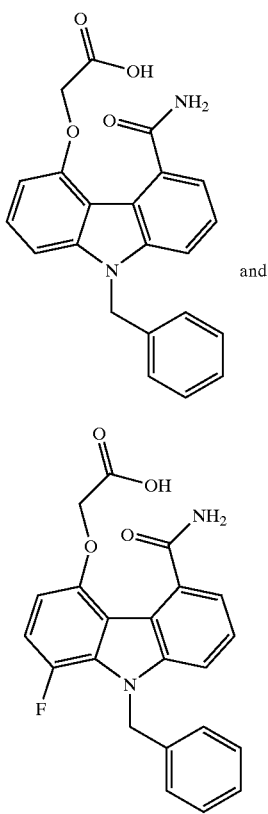

(Xe)

and (XIe)

For all of the above compounds of the carbazole or tetrahydrocarbazole type it is advantageous to use them in their (i) acid form, or (ii) pharmaceutically acceptable (e.g., Na, K) form, or (iii) and prodrugs derivatives (e.g., methyl ester, ethyl ester, n-butyl ester, morpholino ethyl ester).

Prodrugs are derivatives of sPLA$_2$ inhibitors used in the method of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Specific preferred prodrugs are ester prodrugs inclusive of methyl ester, ethyl ester, n-propyl ester, isopropyl ester, n-butyl ester, sec-butyl, tert-butyl ester, N,N-diethylglycolamido ester, and morpholino-N-ethyl ester. Methods of making ester prodrugs are disclosed in U.S. Pat. No. 5,654,326. Additional methods of prodrug synthesis are disclosed in U.S. Provisional Patent Application Serial No. 60/063280 filed Oct. 27, 1997 (titled, N,N-diethylglycolamido ester Prodrugs of Indole sPLA2 Inhibitors), the entire disclosure of which is incorporated herein by reference; U.S. Provisional Patent Application Serial No. 60/063646 filed Oct. 27, 1997 (titled, Morpholino-N-ethyl Ester Prodrugs of Indole sPLA2 Inhibitors), the entire disclosure of which is incorporated herein by reference; and U.S. Provisional Patent Application Serial No. 60/063284 filed Oct. 27, 1997 (titled, Isopropyl Ester Prodrugs of Indole sPLA$_2$ Inhibitors), the entire disclosure of which is incorporated herein by reference.

Process for Making the Compounds used in the Method of the Invention

Carbazole and tetrahydrocarbazole sPLA$_2$ inhibitor compounds useful for practicing the method of the invention may be made by the following general methods:

The compounds of formula Ie where Z is cyclohexene are prepared according to the following reaction Schemes Ig(a) and (c).

Scheme Ig(a)

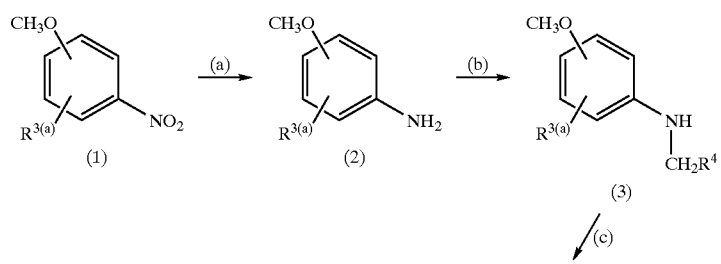

-continued

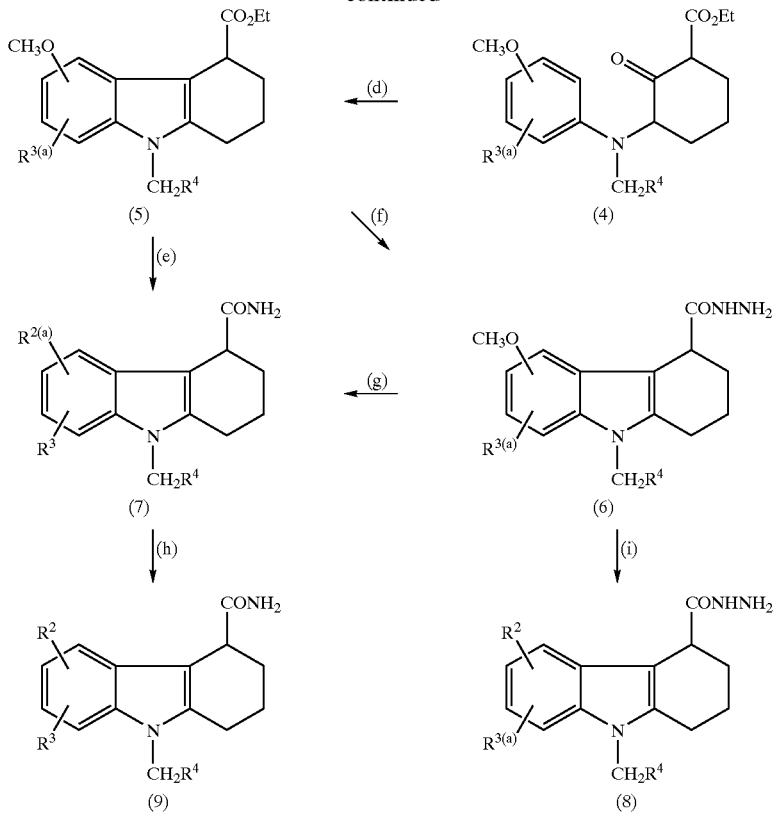

wherein;
- $R^1$ is —$NH_2$, $R^3(a)$ is H, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo, or —$CF_3$; —$CH_2OSi(C_1-C_6)$alkyl, furyl, thiophenyl, —$(C_1-C_6)$hydroxyalkyl, —$(C_1-C_6)$alkoxy$(C_1-C_6)$alkyl, —$(C_1-C_6)$alkoxy$(C_1-C_6)$alkenyl; or —$(CH_2)_nR^8$ where $R^8$ is H, —$CONH_2$, —$NR^9R^{10}$, —CN or phenyl where $R^9$ and $R^{10}$ are independently hydrogen, —$CF_3$, phenyl, —$(C_1-C_4)$alkyl, —$(C_1-C_4)$alkylphenyl or -phenyl$(C_1-C_4)$alkyl and n is 1 to 8;
- when $R^1$ is —$NHNH_2$, $R^3(a)$ is H, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo or —$CF_3$; —$CH_2OSi(C_1-C_6)$alkyl, furyl, thiophenyl, —$(C_1-C_6)$hydroxyalkyl, —$(C_1-C_6)$alkoxy$(C_1-C_6)$alkyl, —$(C_1-C_6)$alkoxy$(C_1-C_6)$alkenyl; or —$(CH_2)_nR^8$ where $R^8$ is H, —$NR^9R^{10}$, —CN or phenyl where $R^9$ and $R^{10}$ are independently hydrogen, —$CF_3$, phenyl, —$(C_1-C_4)$alkyl, —$(C_1-C_4)$alkylphenyl or -phenyl$(C_1-C_4)$alkyl and n is 1 to 8;
- $R^{2(a)}$ is —$OCH_3$ or —OH.

An appropriately substituted nitrobenzene (1) can be reduced to the aniline (2) by treatment with a reducing agent, such as hydrogen in the presence of Pd/C, preferably at room temperature.

Compound (2) is N-alkylated at temperatures of from about 0 to 20° C. using an alkylating agent such as an appropriately substituted aldehyde and sodium cyanoborohydride to form (3). Alternately, an appropriately substituted benzyl halide may be used for the first alkylation step. The resulting intermediate is further N-alkylated by treatment with 2-carbethoxy-6-bromocyclohexanone, preferably at temperatures of about 80° C. to yield (4) or by treatment with potassium hexamethyldisilazide and the bromoketoester.

The product (4) is cyclized to the tetrahydrocarbazole (5) by refluxing with $ZnCl_2$ in benzene for from about 1 to 2 days, preferably at 80° C. (Ref 1). Compound (5) is converted to the hydrazide (6) by treatment with hydrazine at temperatures of about 100° C., or to the amide (7) by reacting with methylchloroaluminum amide in benzene. (Ref 2) Alternatively, (7) may be produced by treatment of (6) with Raney nickel active catalyst.

It will be readily appreciated that when $R^{3(a)}$ is:

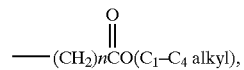

conversion to the amide will also be achieved in this procedure.

Compounds (6) and (7) may be dealkylated, preferably at 0° C. to room temperature, with a dealkylating agent, such as boron tribromide or sodium thioethoxide, to give compound (7) where $R^{2(a)}$ is —OH, which may then be further converted to compound (9), by realkylating with a base, such as sodium hydride, and an alkylating agent, such as $Br(CH_2)_mR^5$, where $R^5$ is the carboxylate or phosphonic diester or nitrile as defined above. Conversion of $R^2$ to the carboxylic acid may be accomplished by treatment with an aqueous base. When $R^2$ is nitrile, conversion to the tetrazole may be achieved by reacting with tri-butyl tin azide or conversion to the carboxamide may be achieved by reacting with basic hydrogen peroxide. When $R^2$ is the phosphonic diester, conversion to the acid may be achieved by reacting with a dealkylating agent such as trimethylsilyl bromide. The monoester may be accomplished by reacting the diester with an aqueous base.

When $R^2$ and $R^3$ are both methoxy, selective demethylation can be achieved by treating with sodium ethanethiolate in dimethylformamide at 100° C. Ref 1 Julia, M.; Lenzi, J. Preparation d'acides tetrahydro-1,2,3,4-carbazole-1 ou-4. *Bull. Soc. Chim. France*, 1962, 2262–2263. Ref 2 Levin, J. I.; Turos, E.; Weinreb, S. M. An alternative procedure for the aluminum-mediated conversion of esters to amides. *Syn. Comm.*, 1982, 12, 989–993.

An alternative synthesis of intermediate (5) is shown in Scheme I(b), as follows.

Scheme Ig(b)

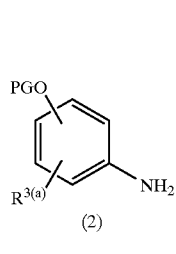

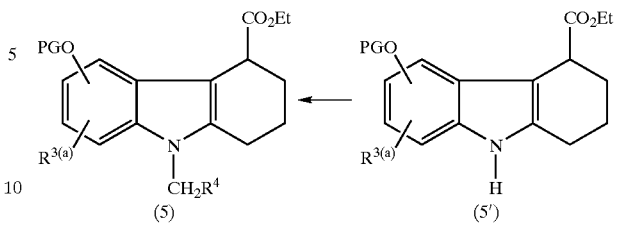

where PG is a protecting group;

$R^{3a}$ is as defined in Scheme 1, above.

The aniline (2) is N-alkylated with 2-carbethoxy-6-bromocyclohexanone in dimethyl formamide in the presence of sodium bicarbonate for 8–24 hours at 50° C. Preferred protecting groups include methyl, carbonate, and silyl groups, such as t-butyldimethylsilyl. The reaction product (4') is cyclized to (5') using the $ZnCl_2$ in benzene conditions described in Scheme I(a), above. N-alkylation of (5') to yield (5) is accomplished by treatment with sodium hydride and the appropriate alkyl halide in dimethylformamide at room temperature for 4–8 hours.

Scheme IIg

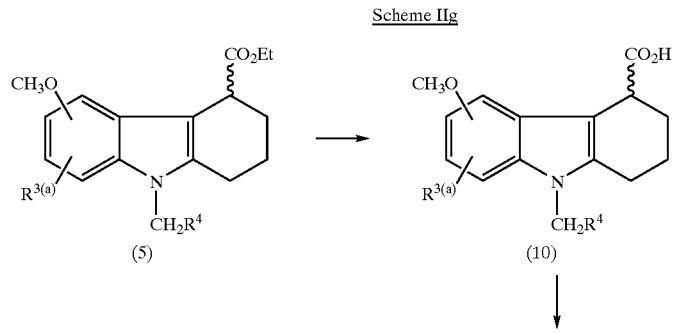

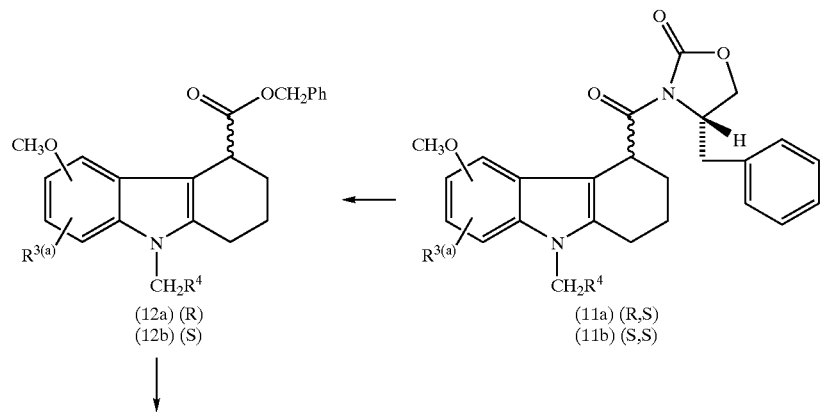

-continued

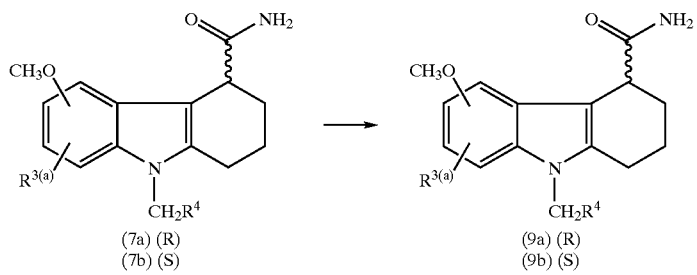

(7a) (R)
(7b) (S)

(9a) (R)
(9b) (S)

$R^{3(a)}$ is as defined in Scheme Ig.

As discussed in Scheme I above, carbazole (5) is hydrolyzed to the carboxylic acid (10) by treatment with an aqueous base, preferably at room temperature to about 100° C. The intermediate is then converted to an acid chloride utilizing, for example, oxalyl chloride and dimethylformamide, and then further reacted with a lithium salt of (S) or (R)-4-alkyl-2-oxazolidine at a temperature of about −75° C., to give (11a) and (11b), which are separable by chromatography.

The diastereomers are converted to the corresponding enantiomeric benzyl esters (12) by brief treatment at temperatures of about 0° C. to room temperature with lithium benzyl oxide. (Ref 3) The esters (12) are then converted to (7) preferably by treatment with methylchloroaluminum amide (Ref 2, above) or, alternately, by hydrogenation using, for example, hydrogen and palladium on carbon, as described above, to make the acid and then reacting with an acyl azide, such as diphenylphosphoryl azide followed by treatment with ammonia. Using the procedure described above in Scheme I, compound (9a) or (9b) may be accomplished. Ref 3 Evans, D. A.; Ennis, M. D.; Mathre, D. J. Asymmetric alkylation reactions of chiral imide enolates. A practical approach to the enantioselective synthesis of alpha-substituted carboxylic acid derivatives. *J. Am. Chem. Soc.*, 1982, 104, 1737–1738.

Compounds of formula Ie where Z is phenyl can be prepared as follows in Schemes III(a)–(f), below.

Scheme III (a)

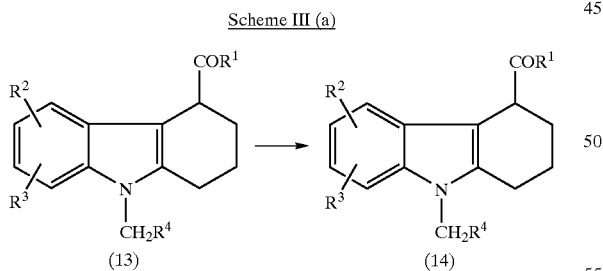

(13)

(14)

A 1,2,3,4-tetrahydrocarbazole-4-carboxamide or 4-carboxhydrazide (13) is dehydrogenated by refluxing in a solvent such as carbitol in the presence of Pd/C to produce the carbazole-4-carboxamide. Alternately, treatment of (13) with DDQ in an appropriate solvent such as dioxane yields carbozole (14).

Depending on the substituent pattern oxidation as described above may result in de-alkylation of the nitrogen. For example when $R^3$ is substituted at the 8-position with methyl, oxidation results in dealkylation of the nitrogen which may be realkylated by treatment with sodium hydride and the appropriate alkyl halide as described in Scheme I(a) above to prepare the deired product (14).

Scheme III(b)

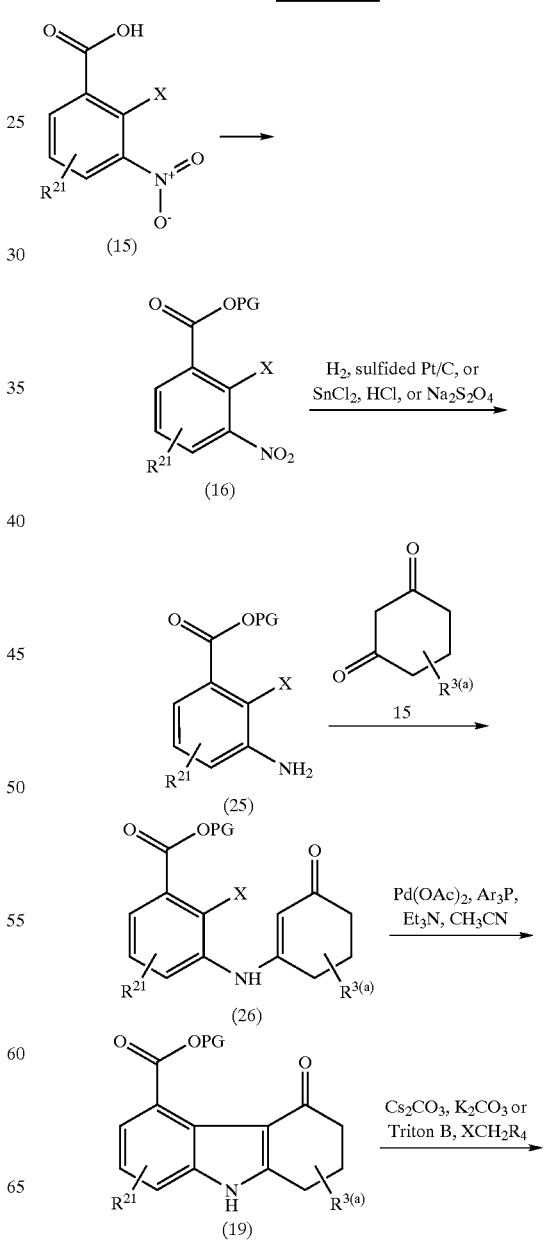

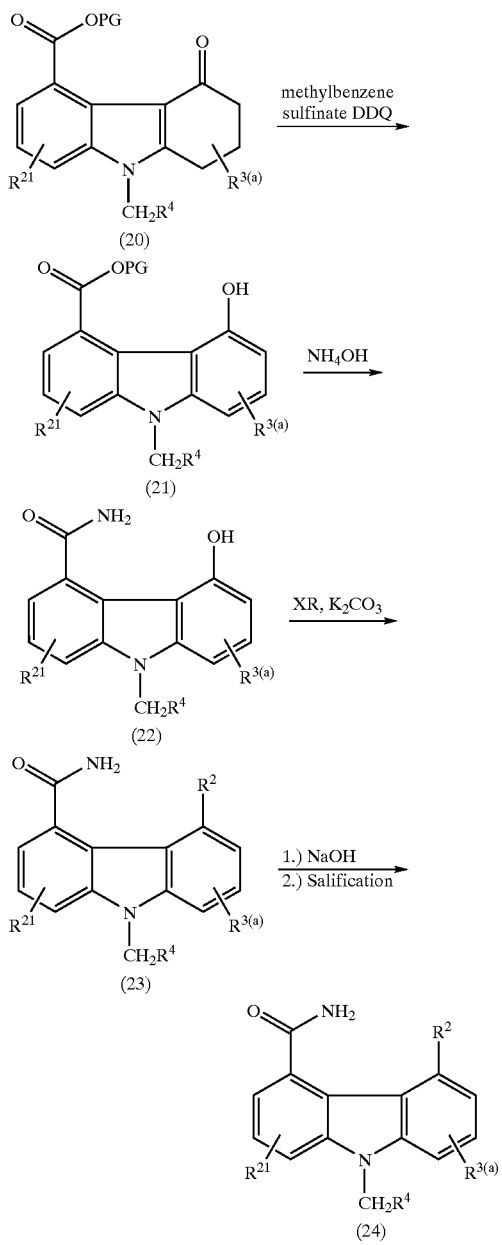

$R^{3(a)}$ is as defined in Scheme I(a) above
PG is an acid protecting group
X is halo Benzoic acid derivative (16) where X is preferably chlorine, bromine or iodine and the protecting group is preferably —CH$_3$, are reduced to the corresponding aniline (25) with a reducing agent, such as stannous chloride in the presence of acid under the general conditions of Sakamoto et al, *Chem Pharm. Bull.* 35 (5), 1823–1828 (1987).

Alternatively, reduction with sodium dithionite in the presence of a base, such as sodium carbonate in a noninterferring solvent, such as water, ethanol, and/or tetrahydrofuran affords starting material (16).

Alternatively, reduction by hydrogenation over a sulfided platinum catalyst supported on carbon with hydrogen at 1 to 60 atmospheres in a noninterferring solvent, preferably ethyl acetate, to form a starting material (16).

The reactions are conducted at temperatures from about 0 to 100° C. preferably at ambient temperature, and are substantially complete in about 1 to 48 hours depending on conditions.

The aniline (25) and dione (15) are condensed under dehydrating conditions, for example, using the general procedure of Iida, et al., (Ref 5), with or without a noninterfering solvent, such as toluene, benzene, or methylene chloride, under dehydrating conditions at a temperature about 10 to 150° C. The water formed in the process can be removed by distillation, azetropic removal via a Dean-Stark apparatus, or the addition of a drying agent, such as molecular sieves, magnesium sulfate, calcium carbonate, sodium sulfate, and the like.

The process can be performed with or without a catalytic amount of an acid, such a p-toluenesulfonic acid or methanesulfonic acid. Other examples of suitable catalysts include hydrochloric acid, phenylsulfonic acid, calcium chloride, and acetic acid.

Examples of other suitable solvents include tetrahydrofuran, ethyl acetate, methanol, ethanol, 1,1,2,2-tetrachloroethane, chlorobenzene, bromobenzene, xylenes, and carbotetrachloride.

The condensation of the instant process is preferably carried out neat, at a temperature about 100 to 150° C. with the resultant water removed by distillation via a stream of inert gas, such as, nitrogen or argon.

The reaction is substantially complete in about 30 minutes to 24 hours.

Intermediate (26) may then be readily cyclized in the presence of a palladium catalyst, such as Pd(OAc)$_2$ or Pd(PPh$_3$)$_4$ and the like, a phosphine, preferably a trialkyl- or triarylphosphine, such as triphenylphosphine, tri-o-tolylphosphine, or tricyclohexylphosphine, and the like, a base, such as, sodium bicarbonate, triethylamine, or diisopropylethylamine, in a noninterfering solvent, such as, acetonitrile, triethylamine, or toluene at a temperature about 25 to 200° C. to form (19).

Examples of other suitable solvents include tetrahydrofuran, benzene, dimethylsulfoxide, or dimethylformamide.

Examples of other suitable palladium catalysts include Pd(PPh$_3$)Cl$_2$, Pd(OCOCF$_3$)$_2$, [(CH$_3$C$_6$H$_4$)$_3$P]$_2$PdCl$_2$, [(CH$_3$CH$_2$)$_3$P]$_2$PdCl$_2$, [(C$_6$H$_{11}$)$_3$P]$_2$PdCl$_2$, and [(C$_6$H$_5$)$_3$P]$_2$PdBr$_2$.

Examples of other suitable phosphines include triisopropylphosphine, triethylphosphine, tricyclopentylphosphine, 1,2-bis(diphenylphosphino) ethane, 1,3-bis(diphenylphosphino)propane, and 1,4-bis (diphenylphosphino)butane.

Examples of other suitable bases include tripropyl amine, 2,2,6,6-tetramethylpiperidine, 1,5-diazabicyclo[2.2.2] octane (DABCO), 1,8-diazabicyclo[5.4.0]undec-7-ene (DBU), 1,5-diazabicyclo[4.3.0]non-5-ene, (DBN) sodium carbonate, potassium carbonate, and potassium bicarbonate.

The cyclization of the instant process is preferably carried out with palladium(II)acetate as catalyst in the presence of either triphenylphosphine, tri-o-tolylphosphine, 1,3-bis (diphenylphosphino)propane, or tricyclohexylphosphine in acetonitrile as solvent and triethylamine as base at a temperature about 50 to 150° C. The reaction is substantially complete in about 1 hour to 14 days.

Alternatively, a preferred process for cyclization consists of the reaction of intermediate (26) with a palladacycle catalyst such as trans-di($\mu$-acetato)-bis[o-(di-o-tolylphosphino)benzyl]dipalladium(II) in a solvent such as dimethylacetamide (DMAC) at 120–140° C. in the presence of a base such as sodium acetate.

Intermediate (19) may be alkylated with an alkylating agent $XCH_2R_4$, where X is halo in the presence of a base to form (20). Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide).

The reaction may or may not be carried out in the presence of a crown ether. Potassium carbonate and Triton B are preferred. The amount of alkylating agent is not critical, however, the reaction is best accomplished using an excess of alkyl halide relative to the starting material.

A catalytic amount of an iodide, such as sodium iodide or lithium iodide may or may not be added to the reaction mixture. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about 10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (20) May by dehydrogenated by oxidation with 2,3-dichloro-5,6-dicyano-1,4-benzoquinone in a noninterfering solvent to form (21).

Suitable solvents include methylene chloride, chloroform, carbon tetrachloride, diethyl ether, methyl ethyl ketone, and t-butyl methyl ether. Toluene, benzene, dioxane, and tetrahydrofuran are preferred solvents. The reaction is carried out at a temperature about 0 to 120° C. Temperatures from 50 to 120° C. are preferred. The reaction is substantially complete in about 1 to 48 hours depending on conditions.

Intermediate (21) may be aminated with ammonia in the presence of a noninterfering solvent to form a(22). Ammonia may be in the form of ammonia gas or an ammonium salt, such as ammonium hydroxide, ammonium acetate, ammonium trifluoroacetate, ammonium chloride, and the like. Suitable solvents include ethanol, methanol, propanol, butanol, tetrahydrofuran, dioxane, and water. A mixture of concentrated aqueous ammonium hydroxide and tetrahydrofuran or methanol is preferred for the instant process. The reaction is carried out at a temperature about 20 to 100° C. Temperatures from 50 to 60° C. are preferred. The reaction is substantially complete in about 1 to 48 hours depending on conditions.

Alkylation of (22) is achieved by treatment with an alkylating agent of the formula $XCH_2R^9$ where X is halo and $R^{70}$ is $—CO_2R^{71}$, $—SO_3R^{71}$, $—P(O)(OR^{71})_2$, or $—P(O)(OR^{71})H$, where $R^{71}$ is an acid protecting group or a prodrug function, in the presence of a base in a noninterfering solvent to form (23). Methyl bromoacetate and t-butyl bromoacetate are the preferred alkylating agents.

Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide). The reaction may or may not be carried out in the presence of a crown ether. Cesium carbonate and Triton B are preferred.

The amount of alkylating agent is not critical, however, the reaction is best accomplished using an excess of alkyl halide relative to the starting material. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about −10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (23) may be optionally hydrolyzed with a base or acid to form desired product (24) and optionally salified.

Hydrolysis of (23) is achieved using a base such as sodium hydroxide, potassium hydroxide, lithium hydroxide, aqueous potassium carbonate, aqueous sodium carbonate, aqueous lithium carbonate, aqueous potassium bicarbonate, aqueous sodium bicarbonate, aqueous lithium bicarbonate, preferably sodium hydroxide and a lower alcohol solvent, such as, methanol, ethanol, isopropanol, and the like. Other suitable solvents include acetone, tetrahydrofuran, and dioxane.

Alternatively, the acid protecting group may be removed by organic and inorganic acids, such as trifluoroacetic acid and hydrochloric acid with or without a noninterferring solvent. Suitable solvents include methylene chloride, tetrahydrofuran, dioxane, and acetone. The t-butyl esters are preferably removed by neat trifluoroacetic acid.

The reaction is conducted at temperatures from about −10 to 100° C. preferably at ambient temperature, and is substantially complete in about 1 to 48 hours depending on conditions.

The starting material (16) is prepared by esterifying compound (15) with a alkyl halide=XPG; where X is halo and PG is an acid protecting group, in the presence of a base, preferably potassium carbonate or sodium cabonate, in a noninterferring solvent, preferably dimethylformamide or dimethylsulfoxide. The preferred alkyl halide is methyl iodide. The reaction is conducted at temperatures from about 0 to 100° C. preferably at ambient temperature, and is substantially complete in about 1 to 48 hours depending on conditions.

Alternatively the starting material (16) may be prepared by condensation with an alcohol HOPG, where PG is an acid protecting group, in the presence of a dehydrating catalyst such as, dicyclohexylcarbodiimide (DCC) or carbonyl diimidazole.

In addition, U.S. Pat. No. 4,885,338 and Jpn. Kokai Tokkyo Koho 05286912, November 1993 Hesei teach a method for preparing 2-fluoro-5-methoxyaniline derivatives.

Scheme IIIg(c)

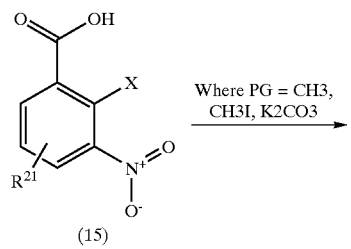

Where PG = CH3, CH3I, K2CO3

(15)

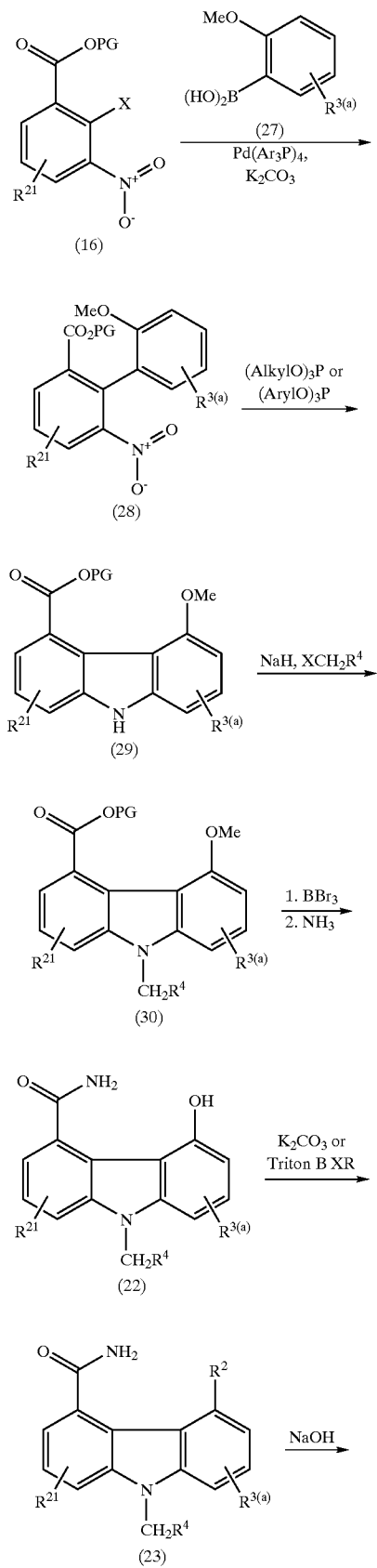

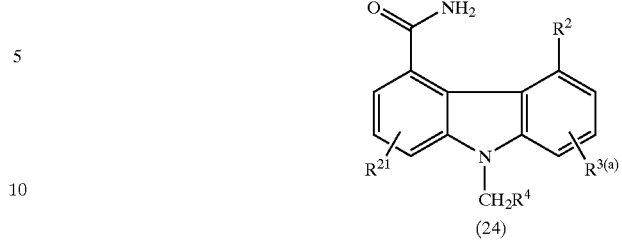

R is as defined in Scheme IIIg(b),
$R^{3(a)}$ is as defined in Scheme Ig(a), above; and
X is halo.

Benzoic acid derivatives (16) (X=Cl, Br, or I) and boronic acid derivative (27) (either commercially available or readily prepared by known techniques from commercially available starting materials) are condensed under the general procedure of Miyaura, et al., (Ref 8a) or Trecourt, et al., (Ref 8b) in the presence of a palladium catalyst, such as $Pd(Ph_3P)_4$, a base, such as sodium bicarbonate, in an inert solvent, such as THF, toluene or ethanol, to afford compound (28).

Compound (28) is converted to the carbazole product (29) by treatment with a trialkyl or triaryl phosphite or phosphine, such as, triethylphosphite or triphenyl phosphine, according to the general procedure of Cadogan, et al. (Ref 6).

Compound (29) is N-alkylated with an appropriately substituted alkyl or aryl halide $XCH_2R^4$ in the presence of a base, such as sodium hydride or potassium carbonate, in a noninterfering solvent, such as toluene, dimethylformamide, or dimethylsulfoxide to afford carbazole (30).

Compound (30) is converted to the corresponding amide (22) by treatment with boron tribromide or sodium thioethoxide, followed by ammonia or an ammonium salt, such as ammonium acetate, in an inert solvent, such as water or alcohol, or with methylchloroaluminum amide in an inert solvent, such as toluene, at a temperature between 0 to 110° C.

When $R^{3(a)}$ is substituted at the 8-position with chloro, de-alkylation of (30) with boron tribromide results in de-benzylation of the nitrogen as described above. Alkylation may be readily accomplished in a two step process. First, an O-alkylation by treatment with a haloalkyl acetate such as methyl bromo acetate using sodium hydride in tetrahydrofuran, followed by N-alkylation using for example a base such as sodium hydride and an appropriately substituted alkyl or aryl halide in dimethoxy formamide. Compound (22) can be converted to product carbazole product (24) as described previously in Scheme IIIg(b) above.

Conversion to the desired prodrug may be accomplished by techniques known to the skilled artisan, such as for example, by treatment with a primary or secondary halide to make an ester prodrug.

Scheme IIIg(d)

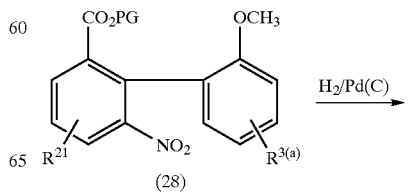

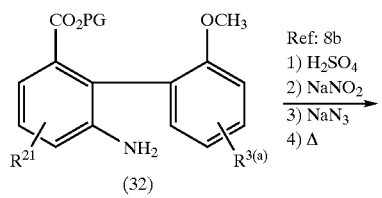

(32)

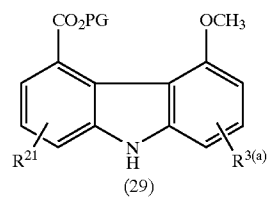

(29)

Alternatively, reduction of the nitro group of compound (28) with a reducing agent, such as hydrogen in the presence of palladium on carbon, in a noninterfering solvent, such as ethanol, at 1 to 60 atmospheres, at a temperature of 0 to 60° C. affords the corresponding aniline (32). Compound (32) is converted to the carbazole (29) according to the general procedure described by Trecourt, et al. (Ref 8b). The aniline is treated with sulfuric acid and sodium nitrite, followed by sodium azide to form an intermediate azide which is cyclized to carbazole (29) by heating in an inert sovent, such as toluene. Compound (29) is converted to carbazole product (24) as described previously in Schemes IIIg(b) and IIIg(c).

References 8) a. N. Miyaura, et al., Synth. Commun. 11, 513 (1981) b. F. Trecourt, et al., Tetrahedron, 51, 11743 6)
6) J. Cadogan et al., J. Chem. Soc., 4831 (1965)

Scheme IIIg(e)

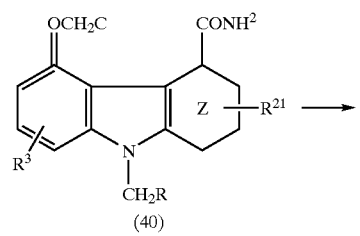

(40)

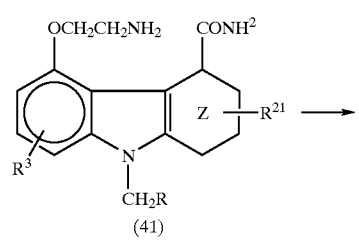

(41)

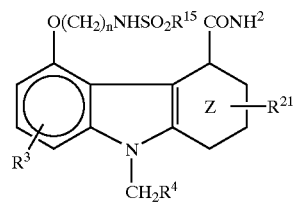

In an aprotic solvent, preferably tetrahydrofuran, reduction of (40) is achieved using a reducing agent such as aluminum trihydride. Preferably, the reaction is conducted under inert atmosphere such as nitrogen, at room temperature.

Sulfonylation may be achieved with an appropriate acylating agent in the presence of an acid scavenger such as triethyl amine.

Scheme IIIg(f)

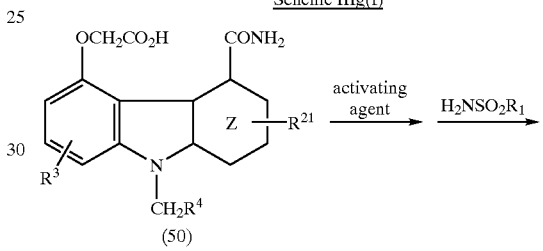

(50)

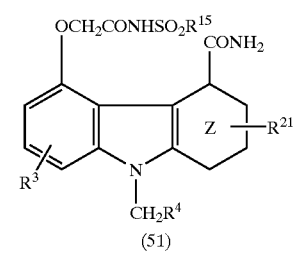

(51)

In a two-step, one-pot process, intermediate (50), prepared as described in Scheme I(a) above, is first activated with an activating agent such as carbonyl diimidazole. The reaction is preferably run in an aprotic polar or non-polar solvent such as tetrahydrofuran. Acylation with the activated intermediate is accomplished by reacting with $H_2NSOR^{15}$ in the presence of a base, preferably diazabicycloundecene.

Scheme IIIg(g)

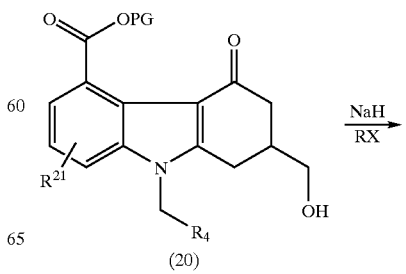

(20)

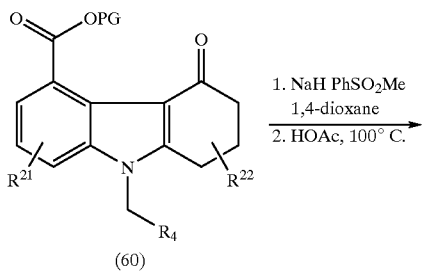

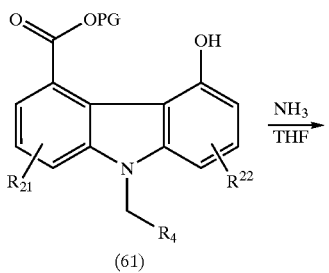

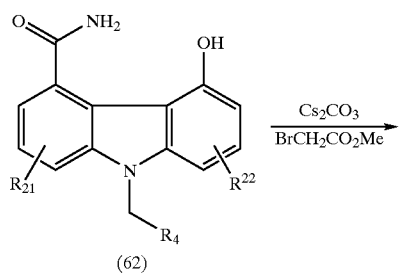

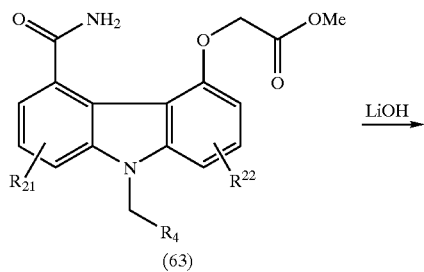

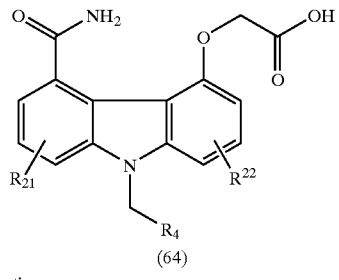

PG is an acid protecting group;
$R^{22}$ is $(C_1-C_6)$alkoxy $(C_1-C_6)$alkyl is $(C_1-C_6)$alkoxy $(C_1-C_6)$alkenyl Starting material (20) is O-alkylated with an alkyl halide or alkenyl halide, using a base such as NaH, in an aprotic polar solvent preferably anhydrous DMF, at ambient temperature under a nitrogen atmosphere. The process of aromatization from a cyclohexenone functionality to a phenol functionality can be performed by treating the tetrahydrocabazole intermediate (60) with a base such as NaH in the presence of methyl benzenesulfinate in an anhydrous solvent, such as 1,4-dioxane or DMF, to form the ketosulfoxide derivative. Upon heating at about 100°C. for 1–2 hours, the ketosulfoxide derivative (60) is converted to the phenol derivative (61). Conversion of the ester (61) to the amide (62) can be achieved by treating a solution of (61) in an aprotic polar solvent such as tetrahydrofuran with ammonia gas. Phenolic O-alkylation of (62) with, for example, methyl bromoacetate can be carried out in anhydrous DMF at ambient temperature using $Cs_2CO_3$ or $K_2CO_3$ as a base to form (63). Desired product (64) can be derived from the basic hydrolysis of ester (63) using LiOH or NaOH as a base in an $H_2O/CH_3OH/THF$ solution at 50° C. for 1–2 hours.

When $R^{22}$ is $—(C_1-C_6)$alkoxy$(C_1-C_6)$alkenyl, hydrogenation of the double bond can be performed by treating (63) in THF using $PtO_2$ as a catalysis under a hydrogen atmosphere. Desired product can then be derived as described above in Scheme III(g) from the basic hydrolysis of ester (63) using LiOH or NaOH as a base in an $H_2O/CH_3OH/THF$ solution at 50° C. for 1–2 hours.

Compounds of formula Ie where the A ring is phenyl and the heteroatom in Z is sulfur, oxygen or nitrogen can be prepared as described in Schemes IV(a)–(f), below.

Scheme Ivg(a)

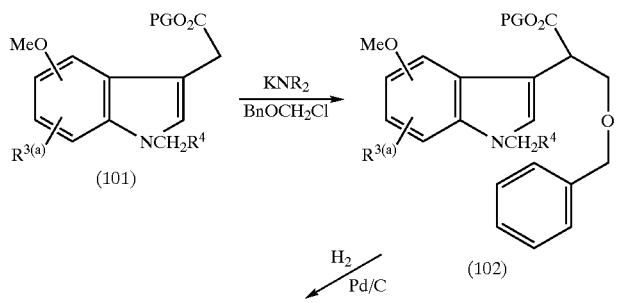

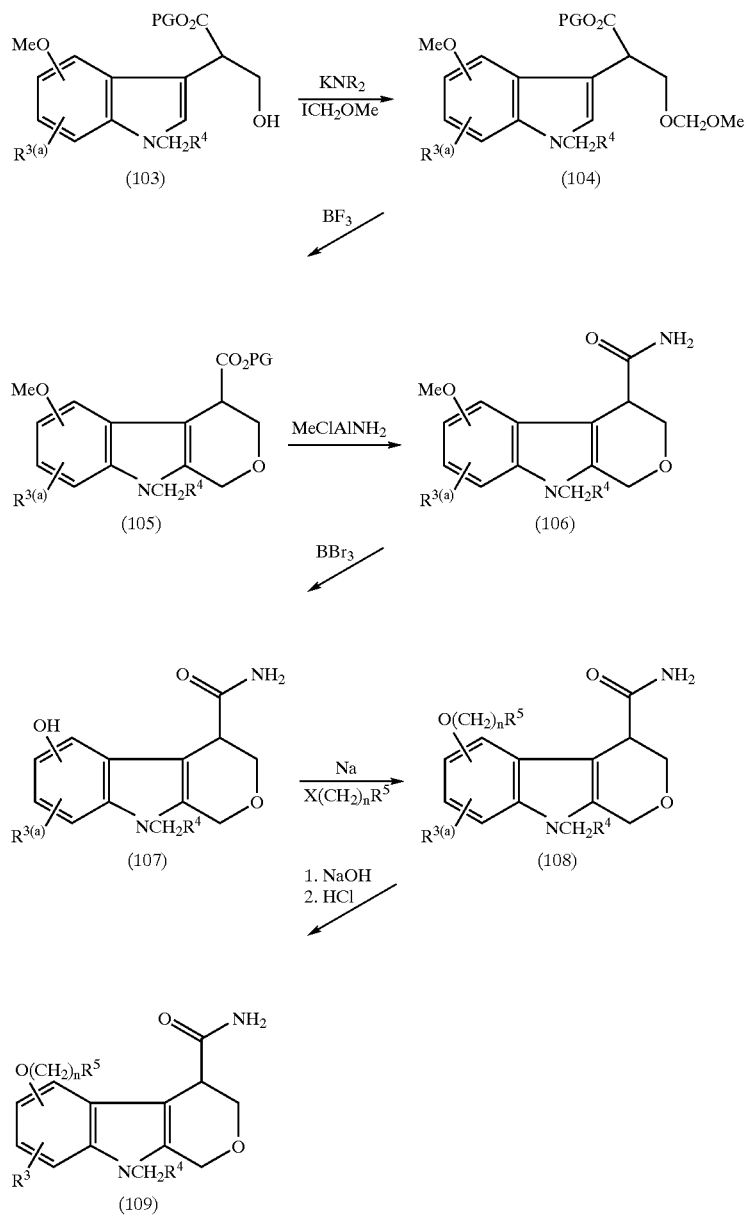

PG is an acid protecting group.

X is halo.

R³(a) is H, —O(C₁–C₄)alkyl, halo, —(C₁–C₆)alkyl, phenyl, —(C₁–C₄)alkylphenyl; phenyl substituted with —(C₁C₆)alkyl, halo or —CF³; —CH₂OSi(C₁–C₆)alkyl, furyl, thiophenyl, —(C₁–C₆)hydroxyalkyl; or —(CH₂)ₙR⁸ where R⁸ is H, —NR⁹R¹⁰, —CN or phenyl where R⁹ and R¹⁰ are independently —(C₁–C₄) alkyl or -phenyl(C₁–C₄)alkyl and n is 1 to 8;

An indole-3-acetic ester (101), Ref 10, is alkylated by treatment with alkalai metal amide and benzyloxymethyl chloride to give (102) which is converted to the alcohol (103) by catalytic hydrogenation. The alcohol is alkylated to provide the formaldehyde acetal (104) which is cyclized by Lewis acid to produce the pyrano[3,4-b]indole (105). The ester is converted to the amide (106) by methylchloroaluminum amide, and then to the phenol (107) with boron tribromide. The phenol is O-alkylated to give (108) which is hydrolyzed to the acid (109).

10) Dillard, R. et al., J, Med Chem. Vol 39, No. 26, 5119–5136.

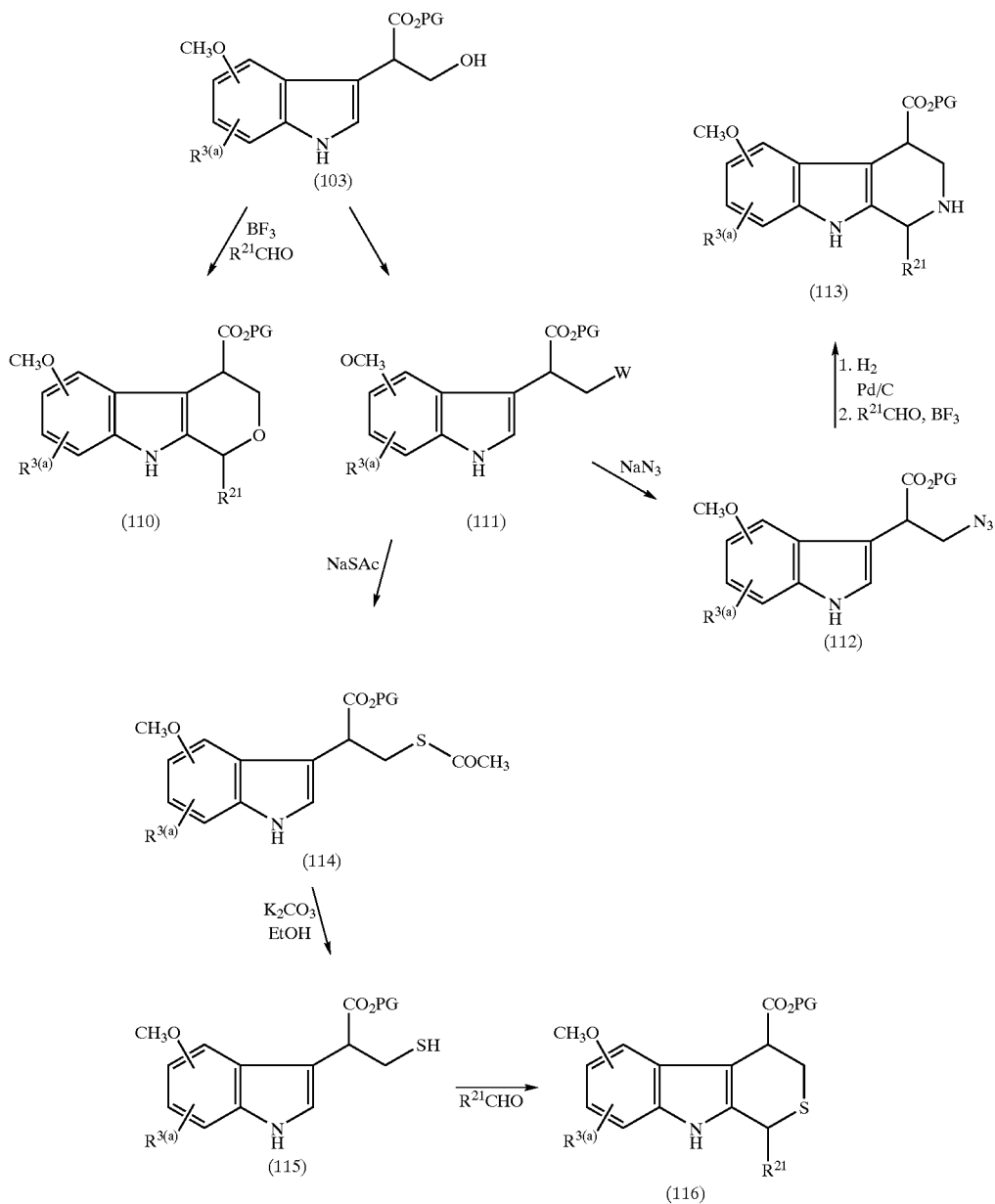

Scheme IVg(b)

PG is an acid protecting group

W is halo, alkyl or aryl sulfonyl $R^3$(a) is H, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo or —$CF^3$; —$CH_2OSi$($C_1$–$C_6$) alkyl, furyl, thiophenyl, —($C_1$–$C_6$)hydroxyalkyl; or —$(CH_2)_n R^8$ where $R^8$ is H, —$NR^9 R^{10}$, —CN or phenyl where $R^9$ and $R^{10}$ are independently —($C_1$–$C_4$)alkyl or -phenyl($C_1$–$C_4$) alkyl and n is 1 to 8;

Reaction of this alcohol (103) with aldehyde and acid produces the pyranoindole (110).

Conversion of the hydroxyl function of (103) to a halide or sulfate functionality is achieved by treatment with triphenylphosphine and $CH_3X$ (where X is a halogen) to make compounds of formula (111) where X is a halide; or by treatment with triethylamine and methanesulfonyl chloride to make the sulfonate. Displacement with the sodium salt of thiol acetic acid gives (114) which in turn is hydrolyzed by base to the thiol (115) which is reacted with an appropriately substituted aldehyde and acid to produce the thiopyranoindoles (116).

Intermediate (111) may also be reacted with sodium azide to give the azido derivative (112) which is reduced by hydrogen catalytically to give the amine which is converted to the carboline (113) with aldehyde and acid.

Intermediates (113), (110) and (116) may be N-alkylated, using sodium hydride and an appropriately substituted alkylhalide $XCH_2 R^4$.

Scheme Ivg(c)
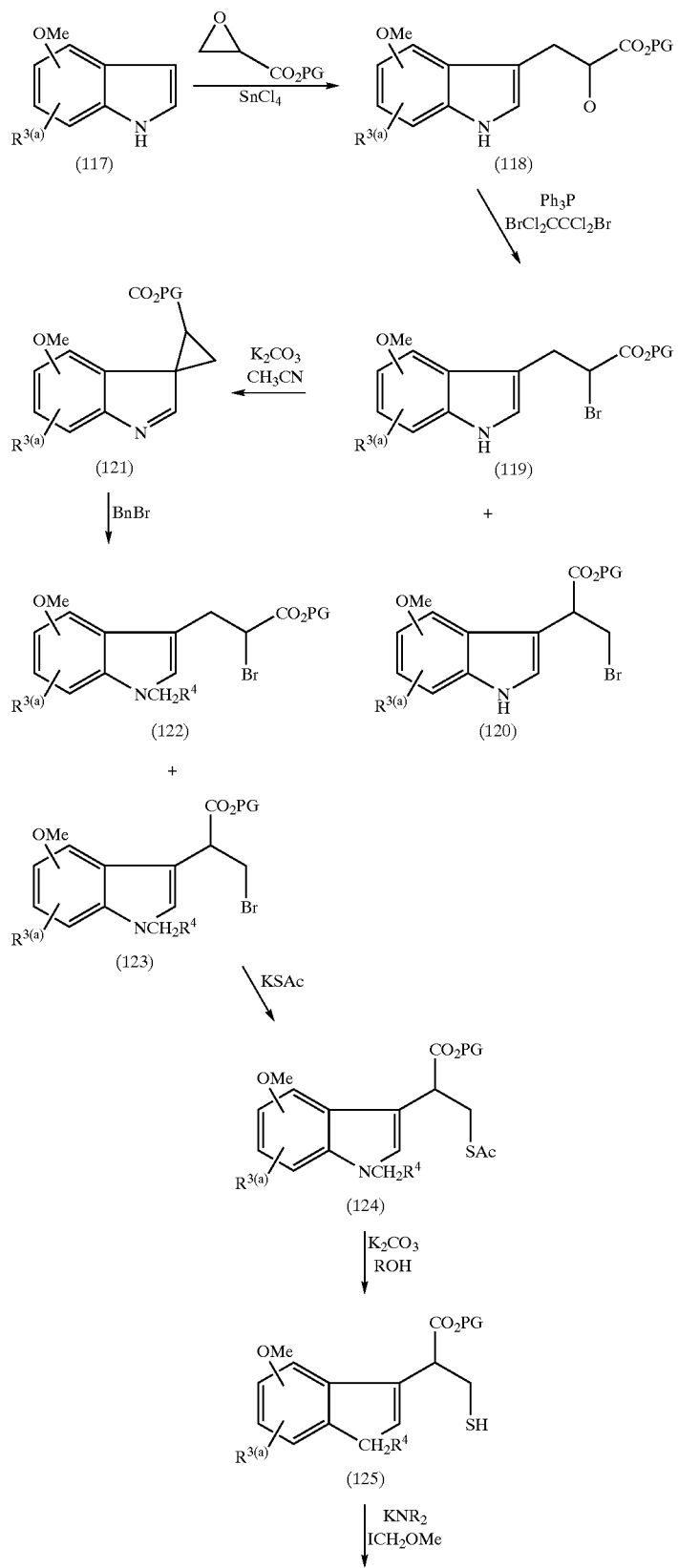

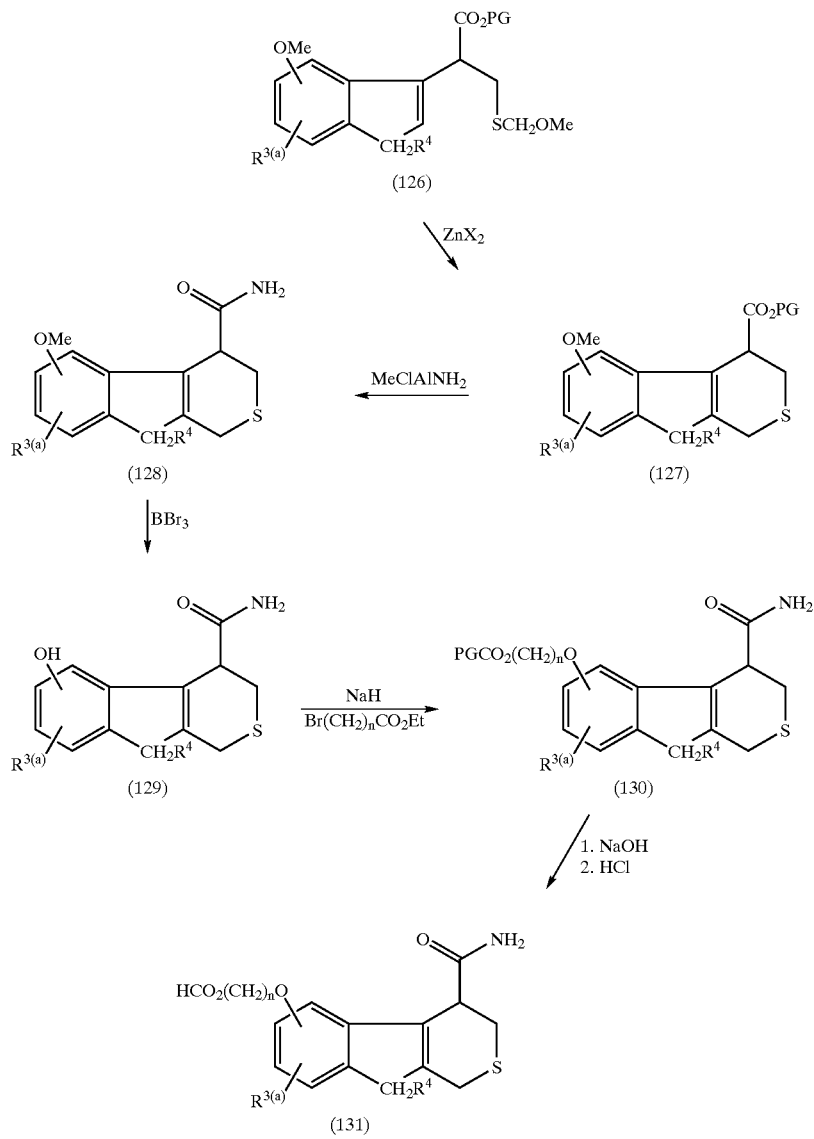

PG is an acid protecting group
$R^{3(a)}$ is as defined above

4-Methoxyindole (117) is converted to the indole acetic acid derivative (118) by alkylation with an epoxy propionate. Treatment of (118) with a brominating reagent affords the mixture of bromo isomers (119) and (120) which give the spiro compound (121) upon basic treatment. Heating (121) with benzyl bromide provides a mixture of the isomeric bromo compounds (122) and (123) which react with potassium thioacetate to give a mixture of isomers from which (124) may be separated. Solvolysis of the thioester produces the thiol (125) which is alkylated to give (126). Lewis acids convert (126) to the thiopyrano[3,4-b]indole (127). The ester function is converted to amide using methylchloroaluminum amide, the methyl ether cleaved by boron tribromide, and the product phenol O-alkylated with bromoacetic ester to give (130) which is hydrolyzed to (131).

Scheme IVg(d)

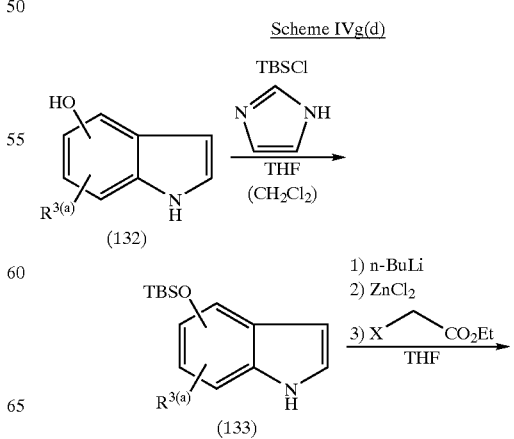

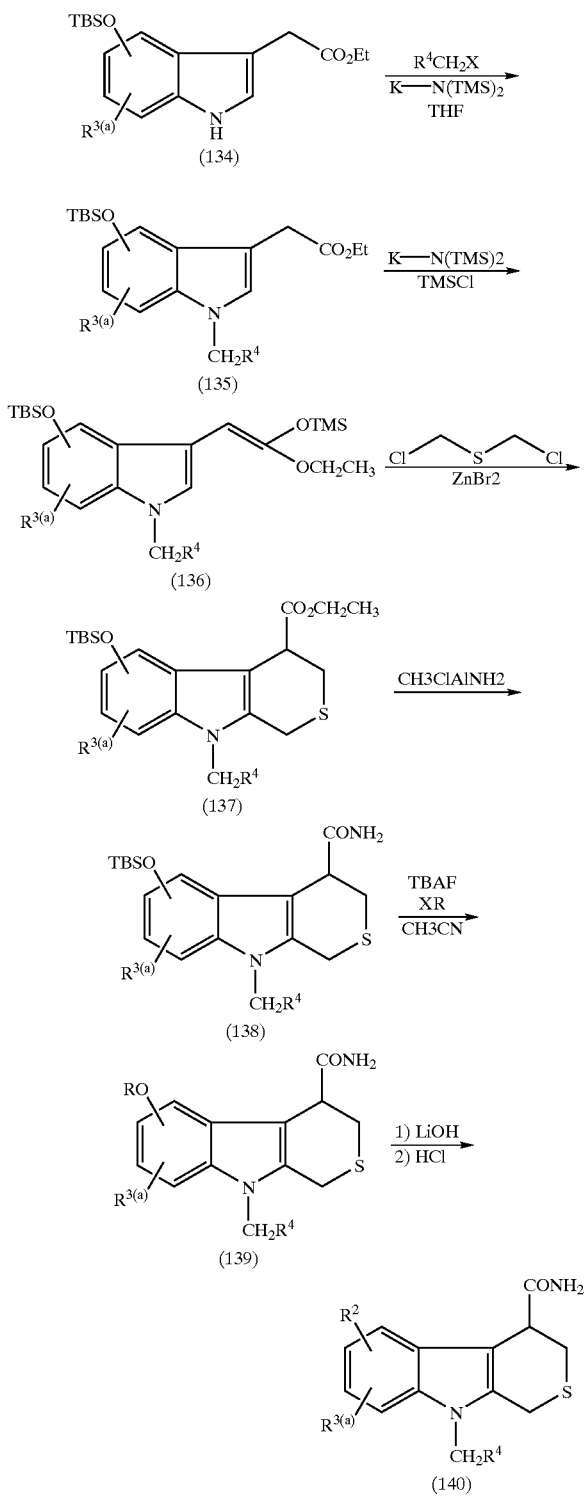

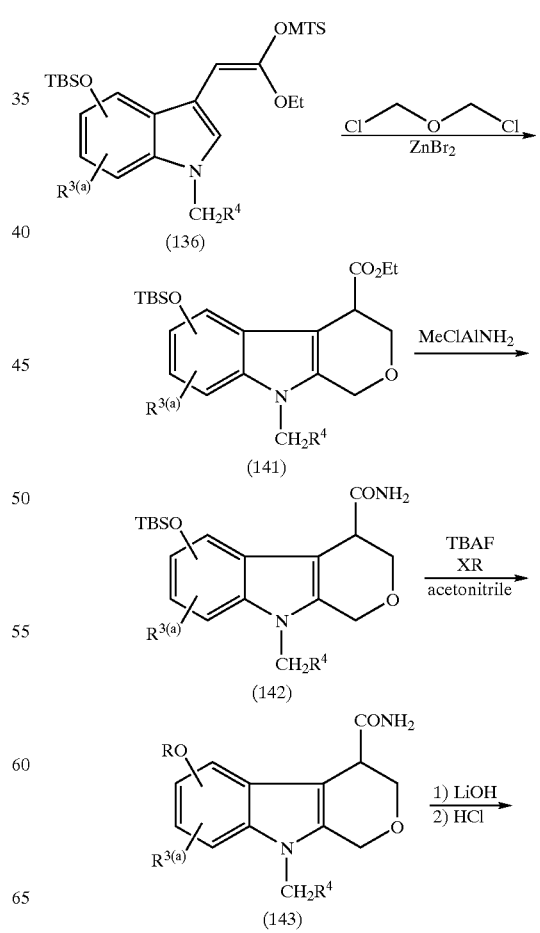

polar solvent such as tetrahydrofuran or methylene chloride accomplishes (133).

Alkylation at the 3-position of the indole (133) is achieved by treatment with n-butyllithium then zinc chloride at temperatures starting at about 10° C. and warming to room temperature, followed by reaction with an appropriate haloalkyl ester such as methyl or ethyl bromoacetate. The reaction is preferably conducted at room temperature in an appropriate aprotic polar solvent such as tetrahydrofuran.

Alkylation of the indole-nitrogen can then be achieved by reacting (134) with a suitable alkyl halide in the presence of potassium bis(trimethylsilyl)amide to prepare (135).

The ester functionality of (135) is converted to a trimethylsilylketene acetal (136) by treatment with potassium bis(trimethylsilyl)amide and trimethylsilyl chloride. Treatment of the ketene acetal (136) with bis(chloromethyl)sulfide and zinc bromide in methylene chloride affords the cyclized product (137). Conversion to amide (138) can be accomplished by a Weinreb reaction with methylchloroaluminum amide. Removal of the oxygen protecting group with a fluoride source, such as tetrabutylammonium fluoride (TBAF), and concommitant reaction of the resulting anion with, for example, ethyl bromoacetate yields the ester (139). Deprotection of the ester yields the desired acid (140).

X is halo,
$R^{3(a)}$ is as defined in Scheme I(a) above; and
R is —$(CH_2)_mR^5$.

Protection of the oxygen by treatment of (132) with tert-butyldimethylsilyl chloride and imidazole in an aprotic

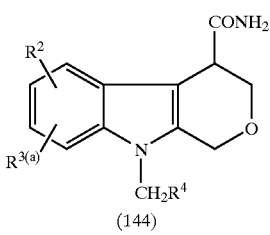

$R^{3(a)}$ is as described in Scheme I(a) and
R is as described in Scheme IV(d).

) is as described in Scheme I(a) and
R is as described in Scheme IV(d).

Treatment of the ketene acetal (136) with bis (chloromethyl)ether and zinc bromide in methylene chloride affords the cyclized product (141). Conversion to amide (142) can be accomplished by a Weinreb reaction with methylchloroaluminum amide. Removal of the oxygen protecting group with a fluoride source, such as tetrabutylammonium fluoride, and concommitant reaction of the resulting anion with ethyl bromoacetate yields the ester (143). Deprotection of the ester yields the desired acid (144).

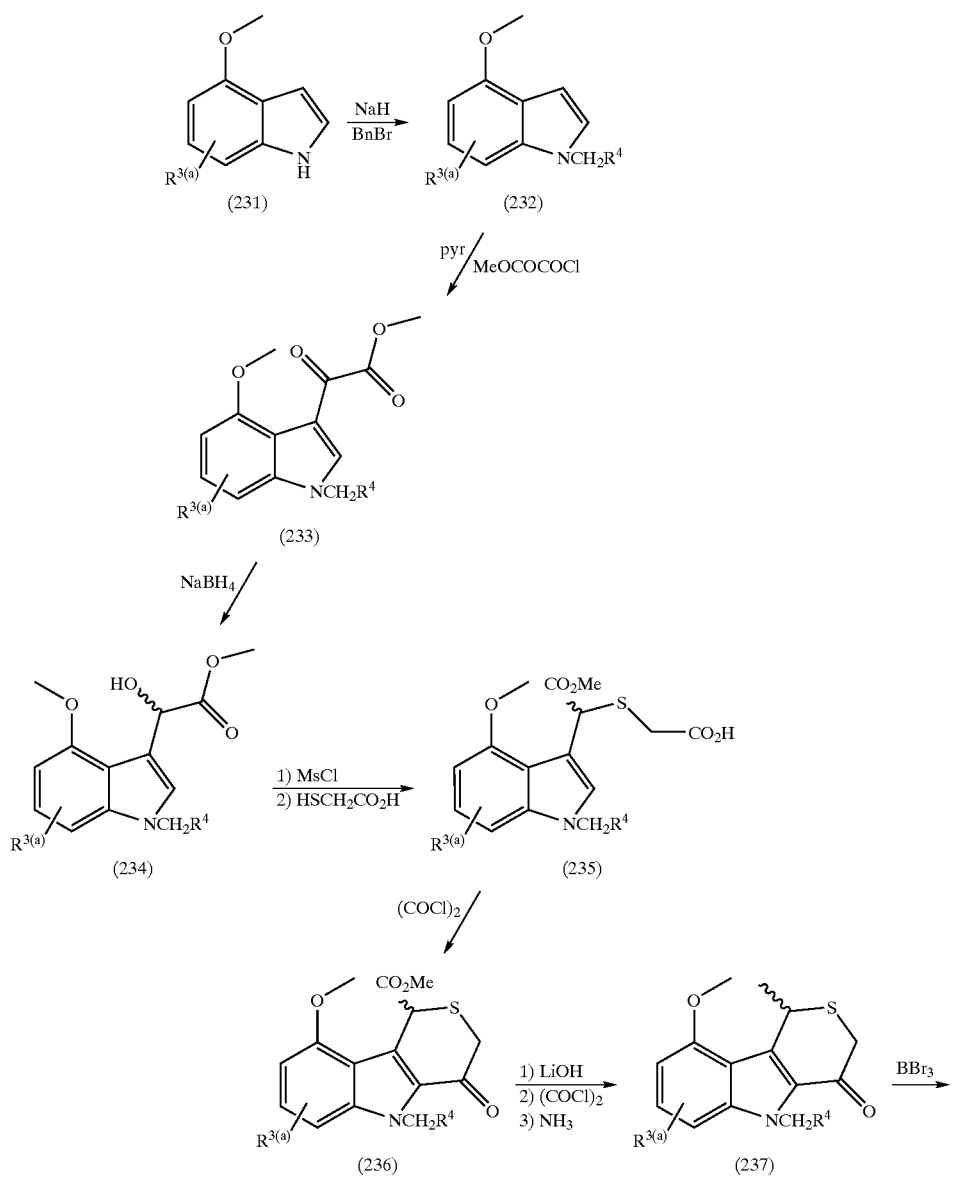

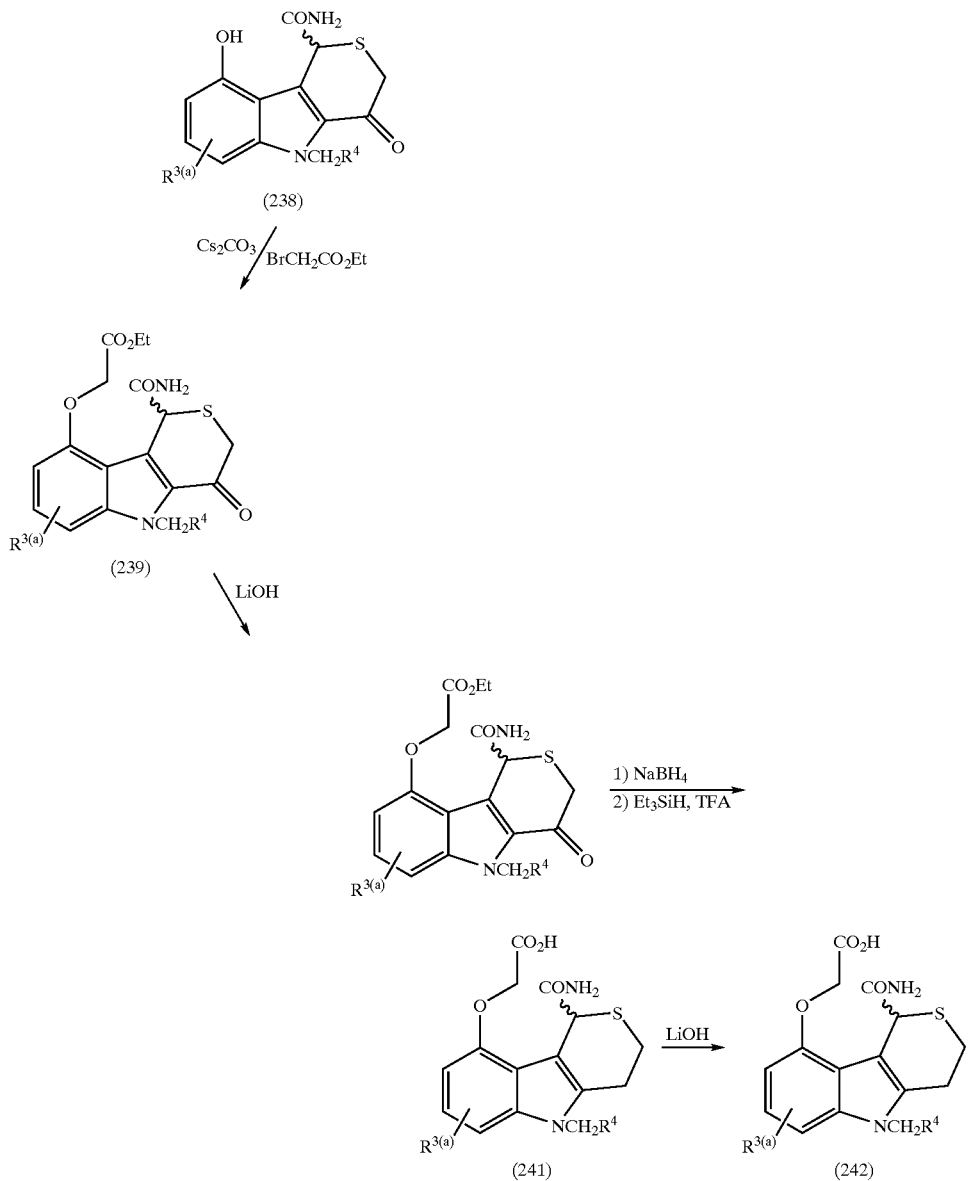

N-alkylation of commercially available 4-methoxy indole (231) under basic conditions using an alkyl halide affords the N-alkyl indole (232). Acylation with a suitable acid chloride provides the glyoxalate ester product (233) which can be reduced with a variety of hydride reducing agents to give intermediate alcohols (234). Conversion of the alcohol to a suitable leaving group and displacement with sulfur nucleophiles affords the thioether product (235). Conversion to the acid chloride and spontaneous cyclization affords the thioketone product (236). Cleavage of the ester can be effected under basic conditions to give the correponding acid which upon formation of the acid chloride and reaction with an appropriate amine gives the amide product (237). Cleavage of the methyl ether gives the phenol (238) which can be alkylated under basic conditions using alkyl halides to give the O-alkylated product (239). Cleavage of the ester under basic conditions gives the desired product (240). Alternatively, reduction of the benzylic ketone with a hydride reducing agent and subsequent deoxygenation of the resulting alcohol gives the deoxygenated product (244). Cleavage of the oxyacetic ester proceeds under basic conditions to give the desired oxyacetic acid (242).

Compounds where Z is an aromatic or heterocyclic ring containing nitrogen can be prepared as described in Schemes Vg(a)–(e), below.

Scheme Vg(a)

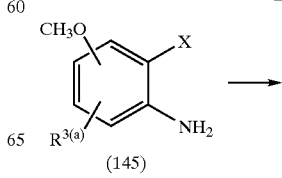

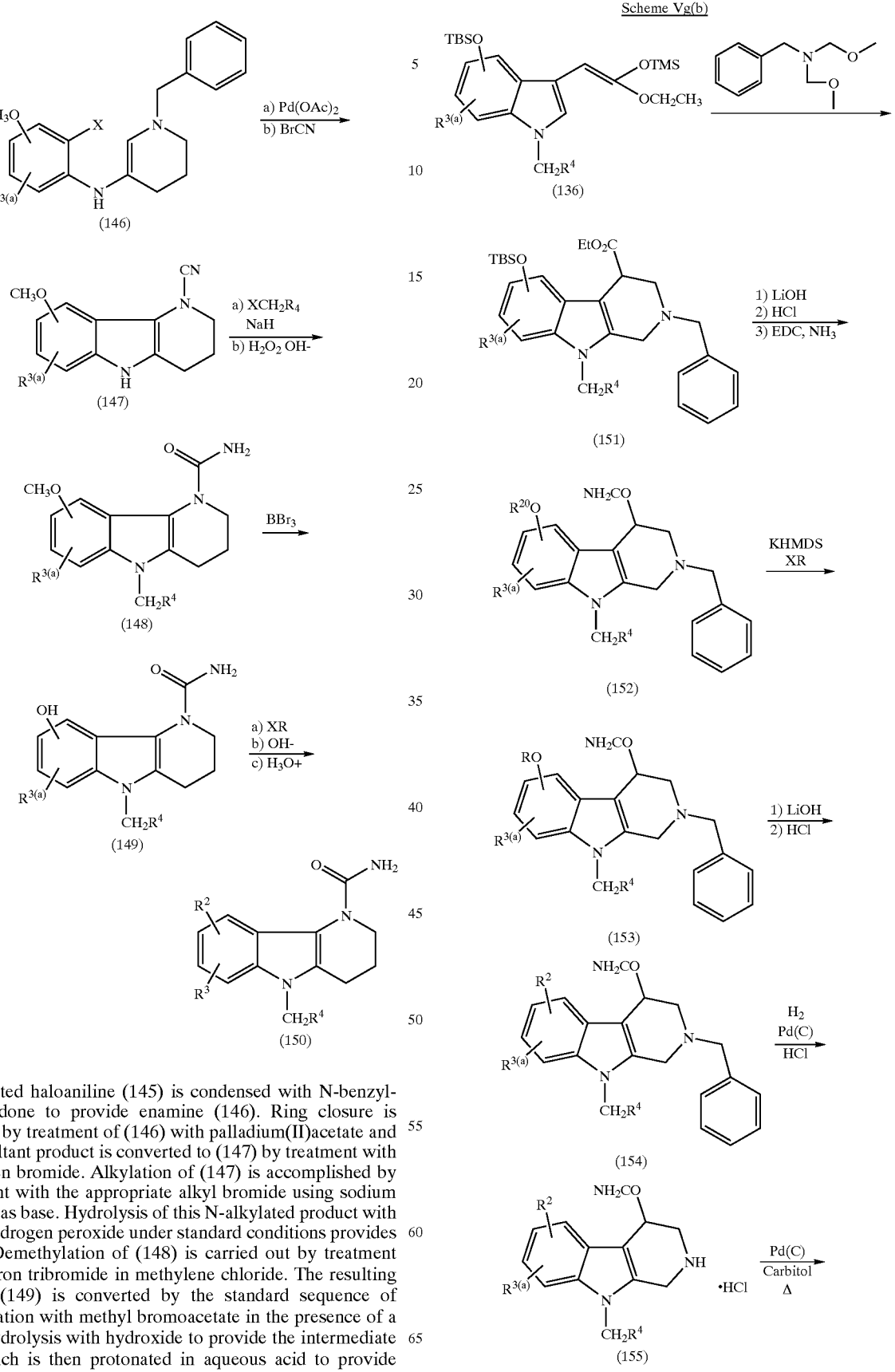

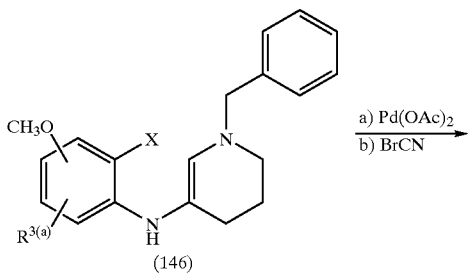

Substituted haloaniline (145) is condensed with N-benzyl-3-piperidone to provide enamine (146). Ring closure is effected by treatment of (146) with palladium(II)acetate and the resultant product is converted to (147) by treatment with cyanogen bromide. Alkylation of (147) is accomplished by treatment with the appropriate alkyl bromide using sodium hydride as base. Hydrolysis of this N-alkylated product with basic hydrogen peroxide under standard conditions provides (148). Demethylation of (148) is carried out by treatment with boron tribromide in methylene chloride. The resulting phenol (149) is converted by the standard sequence of O-alkylation with methyl bromoacetate in the presence of a base, hydrolysis with hydroxide to provide the intermediate salt which is then protonated in aqueous acid to provide desired δ-carboline (150).

-continued

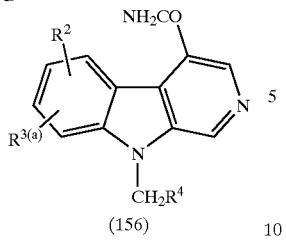

X is halo,
R is as defined in Scheme IV(d), and
R$^{3(a)}$ is as defined in Scheme I(a).

X is halo,

R is as defined in Scheme IV(d), and

R$^{3(a)}$ is as defined in Scheme I(a).

Ketene acetal (136), prepared as described in Scheme IV(d), is reacted with benzyl bis(methoxymethyl)amine in the presence of zinc chloride to give the tetrahydro-beta-carboline (151).

Treatment of (151) with lithium hydroxide, neutralization with hydrochloric acid and subsequent treatment with 1-(3-dimethylaminopropyl)-3-ethylcarbodiimide hydrochloride and ammonia provides the desilyated amide (152) where R$^{20}$ is hydrogen, which can be alkylated with, for example, ethylbromoacetate to give ester (153).

Alternatively, treatment of (115) with the appropriate Weinreb reagent provides amide (152) (R$^{20}$ is t-butyldimethylsilyl) which is desilylated with tetra-n-butylammonium fluoride and alkylated with, for example, ethyl bromoacetate to give ester (153). Lithium hydroxide-mediated hydrolysis gives acid (154), which may be hydrogenated over an appropriate catalyst in the presence of hydrochloride acid to give the tetrahydro-beta-carboline as the hydrochloride salt (155). Compound (155) may in turn be aromatized by refluxing in carbitol with palladium on carbon to provide beta-carboline (156).

Scheme Vg(c)

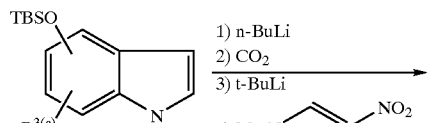

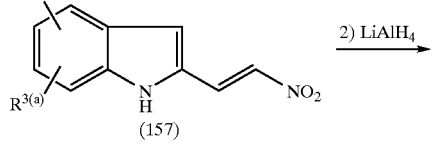

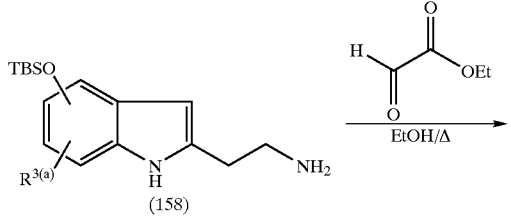

-continued

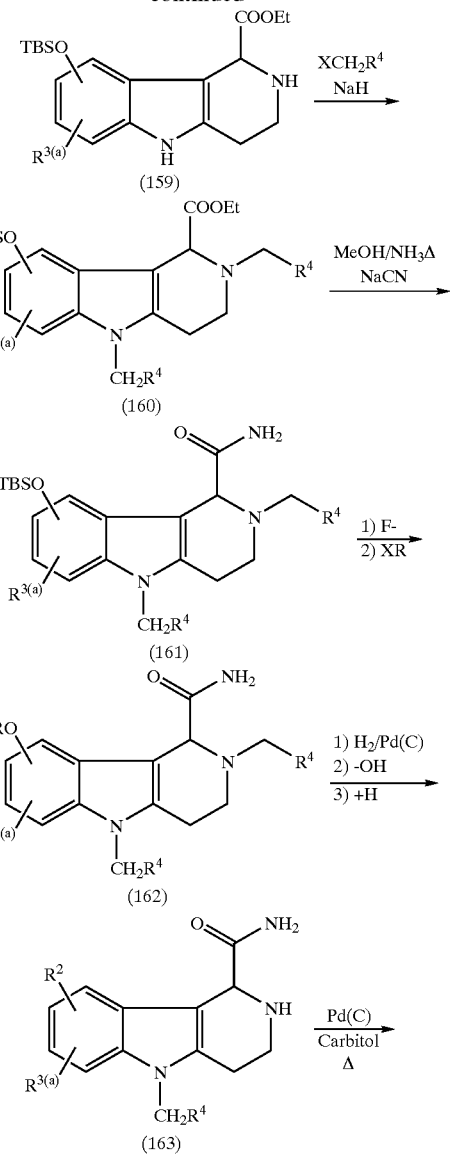

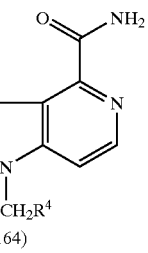

X is halo,
R is as defined in Scheme IV(d); and
R$^{3(a)}$ is as defined in Scheme I(a).

X is halo,

R is as defined in Scheme IV(d); and

R$^{3(a)}$ is as defined in Scheme I(a).

In a one-pot reaction, indole (133) is successively treated with one equivalent n-butyllithium, carbon dioxide gas, one equivalent of t-butyllithium, and 1-dimethylamino-2-nitroethene to give (157). Nitroalkene (157) is reduced with lithium aluminum hydride to amine (158), which is cyclized with methyl glyoxylate (Ref. 9) in refluxing ethanol to give tetrahydrocarboline (159). Alkylation of both nitrogens of (159) leads to intermediate (160), which is treated with the appropriate Weinreb reagent to provide amide (161). Fluoride-assisted desilylation and alkylation with, for example, ethyl iodoacetate gives ester (162), which may be hydrogenated over a suitable catalyst and base-hydrolyzed to give acid (163). Aromatization of (163) to carboline (164) is achieved by refluxing in carbitol in the presence of palladium-on-carbon.

Reference 9

Kelley, T. R.; Schmidt, T. E.; Haggerty, J. G. A convenient preparation of methyl and ethyl glyoxylate, *Synthesis*, 1972, 544–5.

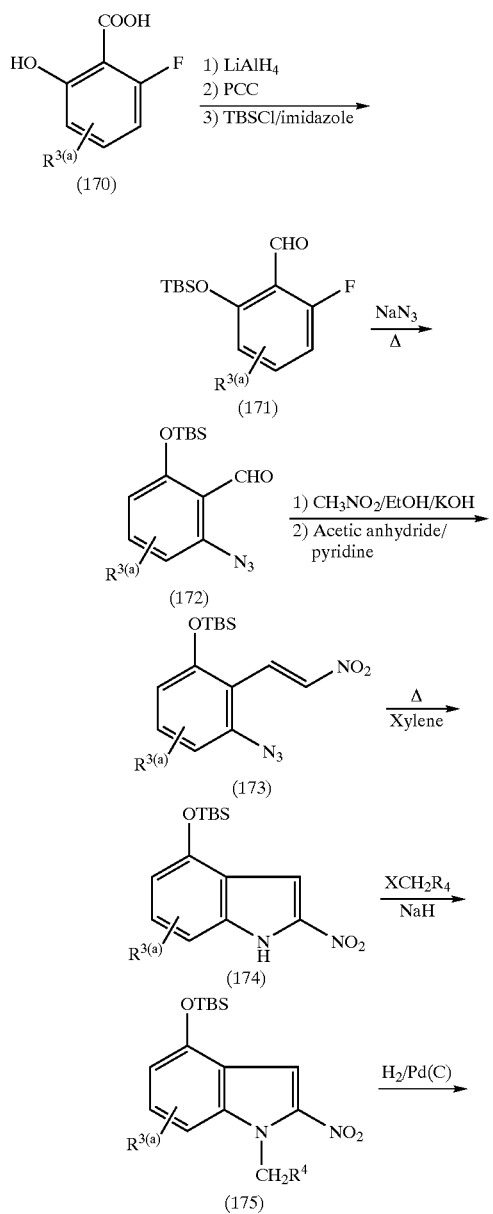

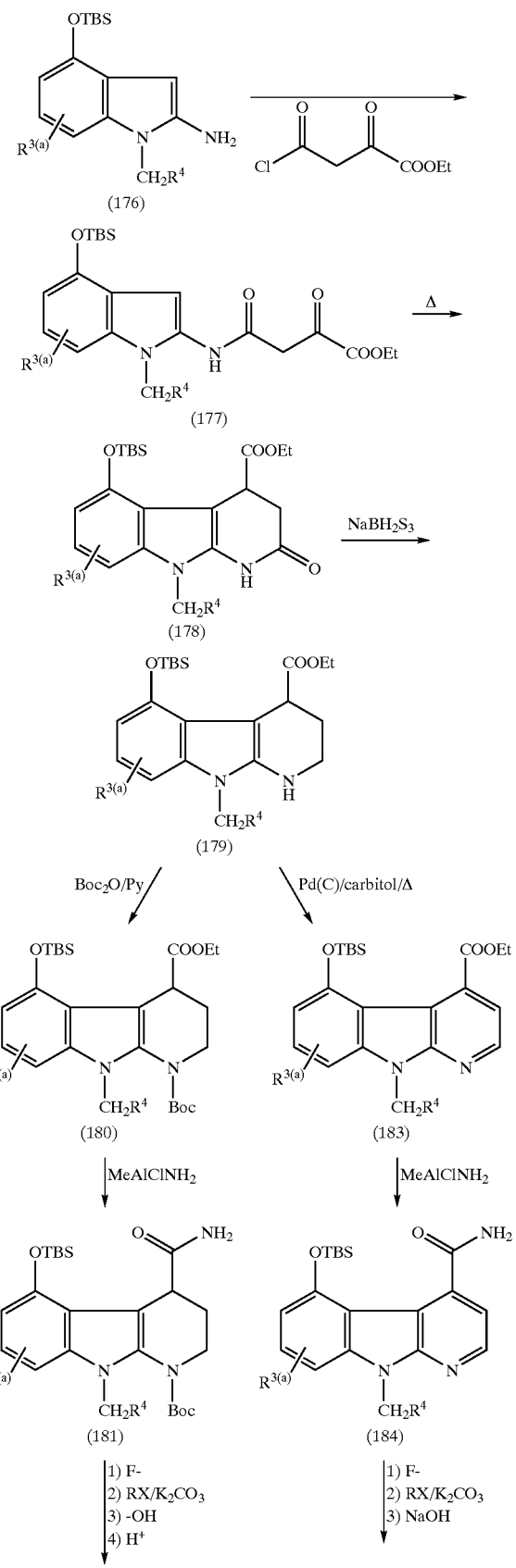

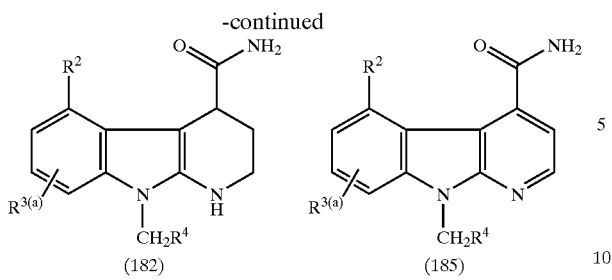

The commercially available acid (170) is reduced with lithium aluminum hydride, oxidized with pyridinium chlorochromate, and silylated with t-butyldimethylsilyl chloride to give (171). Treatment with sodium azide provides azide (172), which is reacted with nitromethane and potassium hydroxide in ethanol, followed by treatment with acetic anhydride and pyridine to give nitroolefin (173). Heating in xylene induces cyclization to produce indole (174). Alkylation with, for example, benzyl iodide and sodium hydride gives (175), which is hydrogenated in the presence of palladium-on-carbon to give amine (176). Acylation with the acid chloride of commercially available oxalacetic acid monoethyl ester gives (177), which is thermally cyclized to lactam (178). Selective reduction of the lactam carbonyl may be accomplished by treatment with $NaBH_2S_3$ to provide amine (179).

Protection of amine (179) with di-t-butyl dicarbonate and pyridine produces (180), which is converted via the appropriate Weinreb reagent to amide (181). Fluoride-assisted desilylation, alkylation with, for example, ethyl iodoacetate and potassium carbonate, base hydrolysis, and acid hydrolysis produce the tetrahydro-alpha-carboline (182).

Alternatively, amine (179) may be aromatized by refluxing in carbitol or some other suitable high boiling solvent to give alpha-carboline (183), which is converted via the appropriate Weinreb reagent to amide (184). Fluoride-assisted desilylation, alkylation with ethyl iodoacetate and potassium carbonate, and base hydrolysis as described above provides alpha-carboline (185).

Scheme Vg(e)

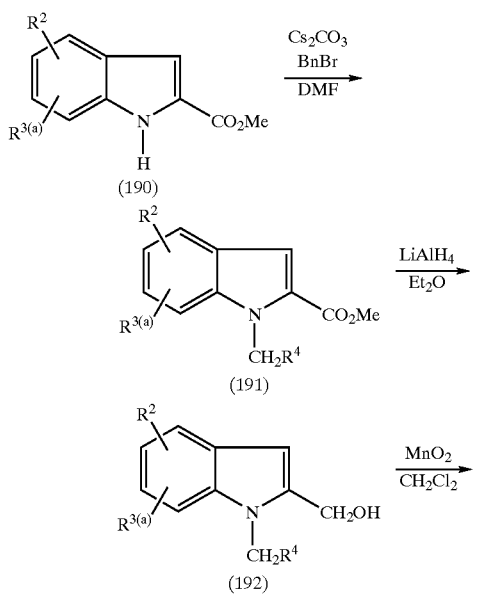

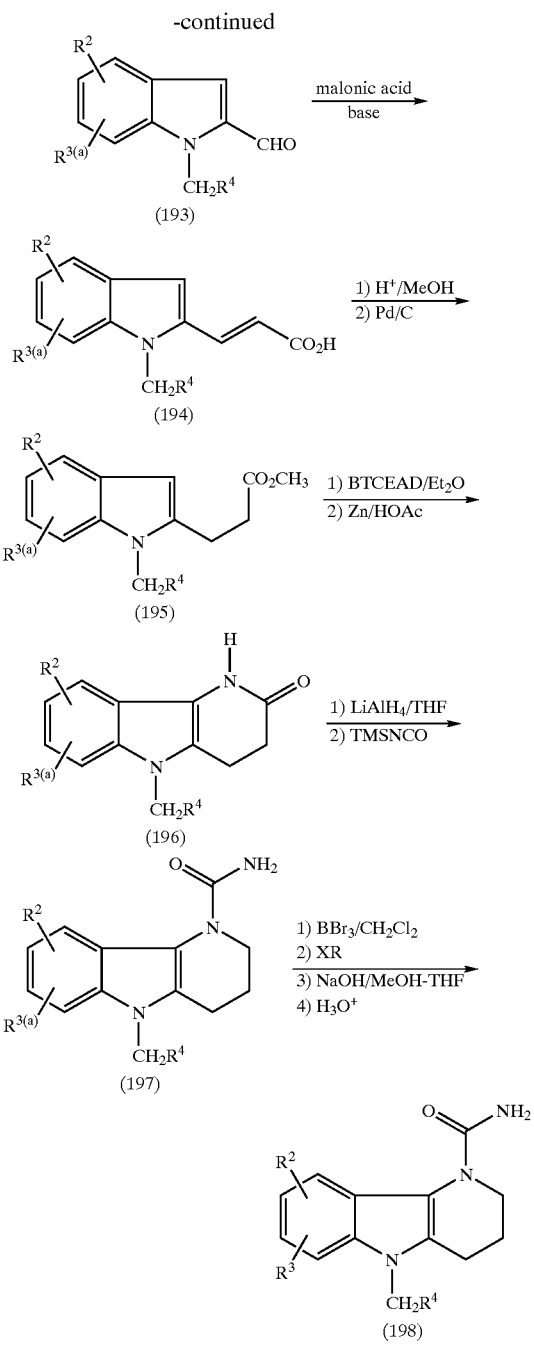

X is halo
$R^{3(a)}$ is as defined above

Scheme V(e) provides δ-carboline (198) by the indicated sequence of reactions. N-alkylation of 2-carboethoxyindole (190) followed by a standard two carbon homologation sequence provides 2-(3-propenoic acid)indoles (194). In this sequence, the condensation of aldehyde (193) with malonic acid utilized a mixture of pyridine and piperidine as the base. After methyl ester formation and hydrogenation (195), ring closure (196) was effected by treatment with bis(2,2,2-trichloroethyl)azodicarboxylate (BTCEAD) followed by zinc in acetic acid. Reduction of the cyclic amide with lithium aluminum hydride followed by treatment with trimethylsilylisocyanate provided the urea (197). Conversion to the desired d-carboline (198) was accomplished under the usual conditions of demethylation and subsequent alkylation and ester hydrolysis steps.

Reverse indoles, i.e., compounds where B is carbon and D is nitrogen can be prepared as described in Scheme VIg, below.

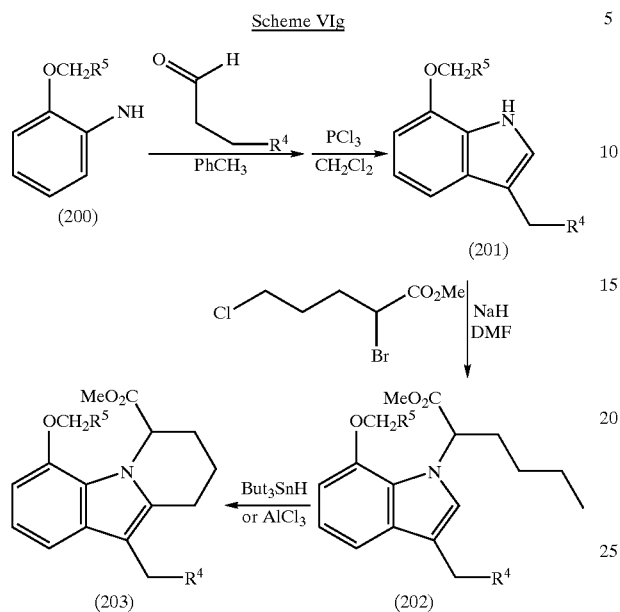

Scheme VIg

Aryl hydrazines (200) are condensed with substituted prpionaldehydes to form hydrazones which are cyclized to indoles (201) by treatment with phosphorous trichloride at room temperature (Ref 1). The indoles are N-alkylated on reaction with a base such as sodium hydride and an alph-bromo ester to give indoles (202) which are cyclized to tetrahydrocarbazoles (203) by Lewis acids (e.g., aluminum chloride) or by radical initiators (e.g., tributyltin hydride). Compounds (203) can be converted to carbazoles by, for example, refluxing in a solvent such as carbitol in the presence of Pd/C.

Compounds of formula I wherein A is pyridyl can be prepared as described in Schemes VIIg(a)–(b), below.

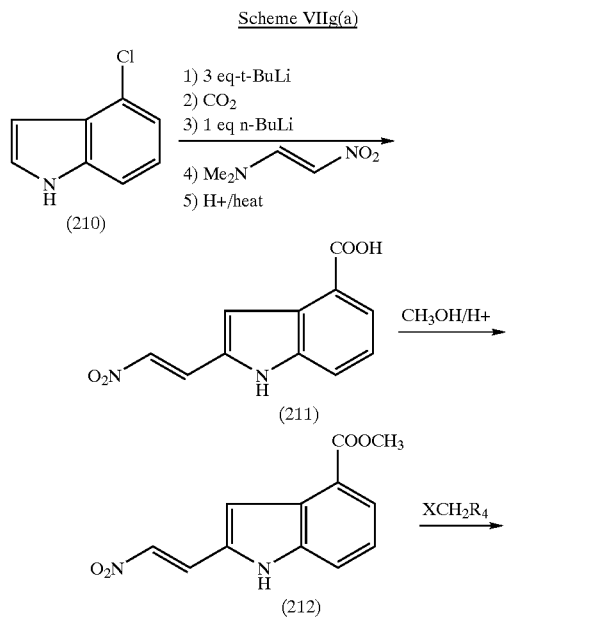

Scheme VIIg(a)

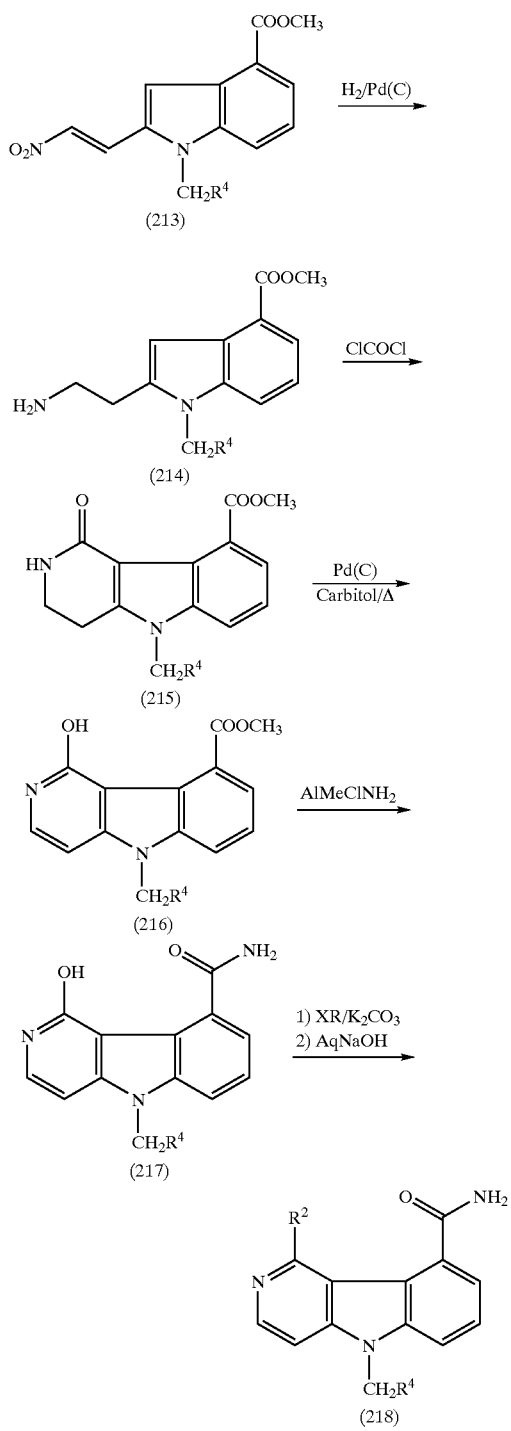

X is halo and
R is $(CH_2)_m R^5$.

Commercially available 4-chloroindole (210) is treated with 3 equivalents of t-butyllithium followed by carbon dioxide, 1 equivalent of n-butyllithium, 1-dimethylamino-2-nitroethene, and acid to provide carboxylic acid (211), which may be esterified to give (212). Alkylation at the 1-position followed by hydrogenation provides aminoethyl indole (214). Cyclization with phosgene to (215) followed by aromatization gives carboline (216). Treatment of (216) with the appropriate Weinreb reagent provides amide (217), which may be alkylated with, for example, ethyl bromoacetate and saponified with sodium hydroxide to give the carboline (218).

Scheme VIIg(b)

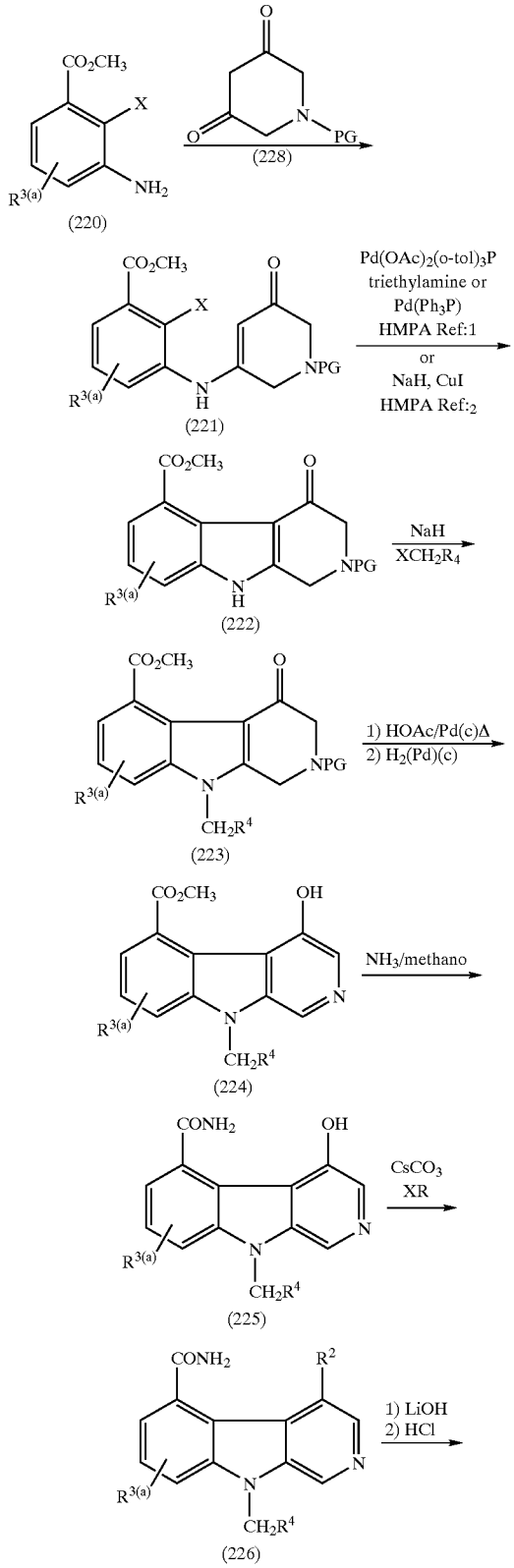

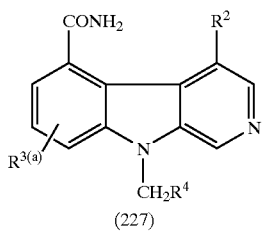

R3(a) is as defined in Scheme I(a),
X is halo, and
R is (CH$_2$)mR$^5$.

The 1,3-dione structures (228) are either commercially available or readily prepared by known techniques from commercially available starting materials. Preparation of the aniline derivatives (220) (X=Cl, Br, or I) are accomplished by reducing an appropriately substituted benzoic acid derivative to the corresponding aniline by treatment with a reducing agent such as SnCl$_2$ in hydrochloric acid in an inert solvent such as ethanol or by hydrogenation using hydrogen gas and sulfided platinum or carbon or palladium on carbon. The amino group of (228) is protected with an appropriate protecting group, such as the, carboethoxyl, benzyl, CBZ (benzyloxycarbonyl) or BOC (tert-butoxycarbonyl) protecting group, and the like.

The dione (228) and aniline derivative (220) are condensed according to the general procedure of Chen, et al., (Ref 10) or Yang, et al., (Ref 11), with or without a noninterfering solvent, such as methanol, toluene, or methylene chloride, with or without an acid, such as p-toluenesulfonic acid or trifluoroacetic acid, with or without N-chlorosuccinimide and dimethyl sulfide, to afford the coupled product (221).

Compound (221) is cyclized under basic conditions with a copper(I)salt in an inert solvent according to the general procedure of Yang, et al., (Ref 8). The derivative (221) is treated with a base, such as sodium hydride, in an inert solvent, such as HMPA, at a temperature between 0 and 25° C. A copper(I)salt, such as copper(I)iodide, is added and the resultant mixture stirred at a temperature between 25 and 150° C. for 1 to 48 hours to afford compound (222).

Compound (221) may also be cyclized according to the general procedure of Chen, et al., (Ref 10). The derivative (221) is treated with a base, such as sodium bicarbonate, and a palladium catalyst, such as Pd(PPh$_3$)$_4$, in an inert solvent, such as HMPA, at a temperature between 25 and 150° C. to afford compound (222).

In a preferred method, intermediate (171) is treated with a transition metal catalyst, such as Pd(OAc)$_2$(O-tol)$_3$P in the presence of a base such as triethylamine using a cosolvent of DMF/acetonitrile to prepare (222).

Compound (222) is N-alkylated with an appropriately substituted benzyl halide in the presence of a base, such as sodium hydride or potassium carbonate, in a noninterfering solvent, such as dimethylformamide or dimethylsulfoxide to afford ketone (223). In a two step, one pot process (222) is aromatized by treatment with acetic acid and palladium on carbon in a noninterfering solvent, such as carbitol or cymene, followed by treatment with hydrogen gas and palladium on carbon to cleave the nitrogen protecting group and produce the phenolic derivative (224).

The ester (224) is converted to the corresponding amide (225) under standard conditions with ammonia (preferably) or an ammonium salt, such as ammonium acetate, in an inert solvent, such as water or alcohol, preferably methanol, or with MeClAlNH$_2$ in an inert solvent, such as toluene, at a temperature between 0 to 110° C. Alkylation of the phenolic oxygen of compound 38 with an appropriate haloester, such as methyl bromoacetate, in the presence of a base, such as cesium carbonate, potassium or sodium carbonate, in an inert solvent, such as dimethylformamide or dimethylsulfoxide affords the ester-amide (226). Other haloesters, such as ethyl bromoacetate, propyl bromoacetate, butyl bromoacetate, and the like can also be used to prepare the corresponding esters.

Saponification of compound (226), with lithium hydroxide in an inert solvent, such as methanol-water, affords (227). The intermediate and final products may isolated and purified by conventional techniques such as chromatography or recrystallization. Regioisomeric products and intermediates can be separated by standard methods, such as, recrystallization or chromatography.

References

10) L.-C. Chen et al., Synthesis 385 (1995)
11) S.-C. Yang et al., Heterocycles, 32, 2399 (1991)

FORMULATIONS USED IN THE METHOD OF THE INVENTION

The substituted tricyclic compound (as described above) may be used at a concentration of 0.1 to 99.9 weight percent of the formulation.

Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration typically contain from about 1 milligram to about 500 milligrams of active compound per unit. In these pharmaceutical compositions the active compound will ordinarily be present in an amount of about 0.5–95% by weight based on the total weight of the composition.

The sPLA$_2$ inhibitors used in the method of the invention may be administered to treat Alzheimer's disease by any means that produces contact of the active compound with the agent's site of action in the human body. The sPLA$_2$ inhibitors can be administered alone, but are generally administered with a pharmaceutical carrier selected on the basis of the chosen route of administration and standard pharmaceutical practice.

Suitable formulations are those comprising a therapeutically effective amount of sPLA$_2$ inhibitor together with a pharmaceutically acceptable diluent or carrier, the composition being adapted for the particular route of administration chosen. By "pharmaceutically acceptable" it is meant the carrier, diluent or excipient must be compatible with the sPLA$_2$ inhibitor ("active compound") in the formulation and not deleterious to the subject being treated.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the sPLA$_2$ inhibitor is mixed with a carrier having the necessary binding properties in suitable proportions and compacted in the shape and size desired.

Sterile liquid form formulations include suspensions, emulsions, syrups and elixirs. The active compound can be dissolved or suspended in a pharmaceutically acceptable carrier, such as sterile water, saline, dextrose solution, sterile organic solvent or a mixture of both.

The active compound can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active compound usually contain suitable carriers, diluents, preservatives, or other excipients, as described in Remington's Pharmaceutical Sciences, Mack Publishing Company, a standard reference text in the field.

Gelatin capsules may be prepared containing the active compound and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

For parenteral solutions, water, a suitable oil, saline, aqueous dextrose (glucose), and related sugar solutions and glycols such as propylene glycol or polyethylene glycols are suitable carriers for parenteral solutions. Solutions for parenteral administration contain the active compound, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Topical ointments, creams, gels, and pastes contain with the active compound diluents such as waxes, paraffins, starch, polyethylene glycol, silicones, bentonites, silicic acid, animal and vegetable fats, talc and zinc oxide or mixtures of these or other diluents.

Topical solutions and emulsions can, for example, contain with the active compound, customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain along with the active compound, the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active compound can be incorporated.

Formulations containing compounds of the invention may be administered through the skin by an appliance such as a transdermal patch. Patches can be made of a matrix such as polyacrylamide and a semipermeable membrane made from a suitable polymer to control the rate at which the material is delivered to the skin. Other suitable transdermal patch formulations and configurations are described in U.S. Pat. Nos. 5,296,222 and 5,271,940, the disclosures of which are incorporated herein by reference. Lipophilic prodrug derivatives of the sPLA$_2$ inhibitors are particularly well suited for transdermal absorption administration and delivery systems.

Formulations within the scope of this invention include the admixture of sPLA2 inhibitor with a other therapeutically effective co-agents for treatment of Alzheimer's disease.

For all of the above formulations the preferred active compound are the substituted tricyclic compounds as previously described (e.g., Formulae I, II, & III).

THE PRACTICE OF THE METHOD OF THE INVENTION

Treatment of Alzheimer's disease in a human may be therapeutic by administering a substituted tricyclic sPLA$_2$ inhibitor to treat an existing condition or prophylactic by administering a substituted tricyclic sPLA$_2$ inhibitor in anticipation of Alzheimer's disease, for example, in a patient whose age, lifestyle, or family history is predictive of the disease.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In general, the sPLA$_2$ inhibitor will be administered to a human so that an effective amount is received. An effective amount may conventionally be determined for an individual patient by administering the active compound in increasing doses and observing the effect on the patient, for example, maintenance of memory and cognitive abilities.

Generally, the compound will typically be administered in a manner and a dose to achieve in the human a blood level concentration of sPLA$_2$ inhibitor of from 100 to 5000 nanograms/ml, and preferably a concentration of 250 to 600 nanograms/ml.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Alternatively, the delivery of hydrophilic drugs may be enhanced by intra-arterial infusion of hypertonic solutions which can transiently open the blood-brain barrier.

The treatment regimen for many Alzheimer's disease may stretch over many years for the remaining life of the patient. Oral dosing is preferred for patient convenience and tolerance. With oral dosing, one to four oral doses per day, each from about 0.01 to 25 mg/kg of body weight with preferred doses being from about 1 mg/kg to about 5 mg/kg.

Parenteral administration (particularly, intravenous administration) is often preferred in instances where rapid alleviation of patient distress is required. With parenteral administration doses of about 0.1 to about 25 mg/kg/day administered continuously or intermittently throughout the day may be used. For parenteral administration, the compound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose).

Inhalation therapy also may be useful either alone or as an adjunct to other routes of administration. With inhalation therapy, doses necessary to produce a decrease in the clinical symptoms of Alzheimer's disease are used.

TESTING METHODS FOR ALZHEIMER'S DISEASE

The diagnostic criteria for Alzheimer's disease are those found in standard medical references (e.g., Harrison's Principles of Internal Medicine, thirteenth ed., 1994, by McGraw-Hill, Inc., ISBN 0-07-032370-4, pgs., 2270–2272). These criteria may be used to determine when to begin using the method of the invention, the frequency and degree of treatment.

A Suitable Assay Protocol for Alzheimer's Disease is found in U.S. Pat. No. 5,686,269 (the disclosure of which is incorporated herein by reference) and may be employed in determining the beginning, duration, and end of treatment by the method of this invention as set out below:

Criteria for the clinical diagnosis of probable Alzheimer's disease include dementia established by clinical examination and documented by the Mini-Mental State Examination, Blessed Dementia Scale, or some similar examination and confirmed by neuropsychologic tests:

a. Deficits in two or more areas of cognition.
b. Progressive worsening of memory and other cognitive functions.
c. No disturbance of consciousness.
d. Onset between ages 40 and 90.
e. Absence of systemic disorders or other brain diseases that could account for the progressive deficits in memory and cognition.

The diagnosis of probable Alzheimer's disease is supported by;

a. Progressive deterioration of specific cognitive functions such as language (aphasia), motor skills (apraxia), and perception (agnosia).
b. Impaired activities of daily living and altered patterns of behavior.
c. Family history of similar disorders, particularly if confirmed neuropathologically.
d. Laboratory results as follows: normal lumbar puncture as evaluated by standard techniques; normal pattern or nonspecific changes in EEG, such as increased slow-wave activity; and evidence of cerebral atrophy on CT with progression documented by serial observation.

Other clinical features consistent with the diagnosis of probable Alzheimer's disease, after exclusion of causes of dementia other than Alzheimer's disease, include;

Plateaus in the course of progression of the illness.

Associated symptoms of depression, insomnia, incontinence, delusions, illusions, hallucinations, sexual disorders, weight loss, and catastrophic verbal, emotional, or physical outbursts.

Other neurologic abnormalities in some patients, especially with more advanced disease and including motor signs such as increased muscle tone, myoclonus, or gait disorder.

Seizures in advanced disease

CT normal for age

Features that make the diagnosis of probable Alzheimer's disease uncertain or unlikely include:

a. Sudden, apoplectic onset.

b. Focal neurologic findings such as hemiparesis, sensory loss, visual field deficits, and incoordination early in the course of the illness.

c. Seizures or gait disturbances at the onset or very early in the course of the illness.

Clinical diagnosis of possible Alzheimer's disease may be on the basis of the dementia syndrome, in the absence of other neurologic, psychiatric, or systemic disorders sufficient to cause dementia and in the presence of variations in the onset, presentation, or clinical course.

Clinical diagnosis of possible Alzheimer's disease may also be made in the presence of a second systemic or brain disorder sufficient to produce dementia such as a. Familial occurrence b. Onset before age 65 c. Presence of trisomy 21 d. Coexistence of other relevant conditions, such as Parkinson's disease nNote:
nNINCDS=National Institute of Neurological and Communicative Disorders and Stroke;
nADRDA=Alzheimer's Disease and Related Disorders Association Under the current standards established by the Consortium to Establish a Registry for Alzheimer's Disease (CERAD), a post-mortem diagnosis of definite AD involves a series of histopathologic tests on biological samples obtained from the patient.

Another suitable Assay Protocol for Alzheimer's Disease is found in U.S. Pat. No. 5,686,476 (the disclosure of which is incorporated herein by reference)and may be employed in determining the beginning, duration, and end of treatment by the method of this invention as set out below:

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo.

The patients are benchmarked as to memory, cognition, reasoning, and other symptoms associated with AD. Women in the test group receive a therapeutically effective dose of sPLA2 inhibitor each day. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an attenuation of the typical cognitive decline and/or behavioral disruptions associated with AD.

Utility of the sPLA2 inhibitor compounds for treatment of Alzheimer's disease is evidenced by activity in this assay protocol.

While the present invention has been illustrated above by certain specific embodiments, these are not intended to limit the scope of the invention as described in the appended claims.

I claim:

1. A method for treating a mammal, including a human, susceptible to having Alzheimer's disease, to prevent or delay the onset of Alzheimer's disease; said method comprising administering to said mammal a prophylactically effective amount of a substituted tricyclic sPLA$_2$ inhibitor represented by the formula (III);

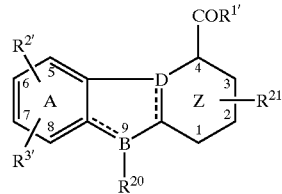

(III)

wherein

A is phenyl or pyridyl wherein the nitrogen is at the 5-, 6-, 7- or 8-position;

one of B or D is nitrogen and the other is carbon;

Z is cyclohexenyl, phenyl, pyridyl, wherein the nitrogen is at the 1-, 2- or 3-position, or a 6-membered heterocyclic ring having one heteroatom selected from the group consisting of sulfur or oxygen at the 1-, 2- or 3-position, and nitrogen at the 1-, 2-, 3- or 4-position;

==== is a double or single bond;

$R^{20}$ is selected from groups (a), (b) and (c) where;

(a) is —($C_5$–$C_{20}$)alkyl, —($C_5$–$C_{20}$)alkenyl, —($C_5$–$C_{20}$)alkynyl, carbocyclic radicals, or heterocyclic radicals, or (b) is a member of (a) substituted with one or more independently selected non-interfering substituents; or (c) is the group —(L)—$R^{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) and carbon, hydrogen, and oxygen only; and where $R^{80}$ is a group selected from (a) or (b);

$R^{21}$ is a non-interfering substituent;

$R^{1'}$ is —NHNH$_2$ or —NH$_2$;

$R^{2'}$ is selected from the group —OH, —O(CH$_2$)$_t R^5$ where $R^5$ is CN or phenyl, or —(L$_a$)-(acidic group); wherein —(L$_a$)— is an acid linker having an acid linker length of 1 to 7 and t is 1–5;

$R^{3'}$ is selected from non-interfering substituent, carbocyclic radicals, carbocyclic radicals substituted with noninterfering substituents, heterocyclic radicals, and heterocyclic radicals substituted with non-interfering substituents;

or a pharmaceutically acceptable salt, racemate, solvate, tautomer, optical isomer or prodrug derivative thereof;

provided that when $R^{3'}$ is H, $R^{20}$ is benzyl and m is 1 or 2, $R^{2'}$ cannot be —O(CH$_2$)$_m$H;

and when D is nitrogen, the heteroatom of Z is selected from the group consisting of sulfur or oxygen at the 1-, 2- or 3-position and nitrogen at the 1-, 2-, 3- or 4-position.

2. The method of claim 1 wherein the substituted tricyclic sPLA$_2$ inhibitor is selected from the following:

4-[(9-benzyl-4-carbamoyl-1,2,3,4-tetrahydrocarbazol-6-yl)oxy]butyric acid; 3-[(9-benzyl-4-carbamoyl-1,2,3,4-tetrahydrocarbazol-6-yl)oxy]propylphosphonic acid; 2-[(9-benzyl-4-carbamoyl-1,2,3,4-tetrahydrocarbazol-6-yl)oxy]methylbenzoic acid; 3-[(9-benzyl-4-carbamoyl-7-noctyl-1,2,3,4-tetrahydrocarbazol-6-yl)oxy]propylphosphonic acid; 4-[(9-benzyl-4-carbamoyl-7-ethyl-1,2,3,4-tetrahydrocarbazol-6-yl)oxy]butyric acid; 3-[(9-benzyl-4-carbamoyl-7-ethyl-1,2,3,4-tetrahydrocarbazol-6-yl)oxy]propylphosphonic acid; 3-[(9-benzyl-4-carbamoyl-7-ethyl-1,2,3,4-tetrahydrocarbazol-6-yl)oxy]propylphosphonic acid; (S)-(+)-4-[(9-benzyl-4-carbamoyl-7-ethyl-1,2,3,4-tetrahydrocarbazol-6-yl)oxy]butyric acid; 4-[9-benzyl-4-carbamoyl-6-(2-cyanoethyl)-1,2,3,4-tetrahydrocarbazol-6-yl)oxybutyric acid; 4-[9-benzyl-4-carboxamido-7-(2-phenylethyl)-1,2,3,4-tetrahydrocarbazol-6-yl]oxybutyric acid; 4-[9-benzyl-4-carboxamidocarbazol-6-yl]oxybutyric acid; methyl 2-[(9-benzyl-4-carbamoyl-1,2,3,4-tetrahydrocarbazol-6-yl)oxy]methylbenzoate; 9-benzyl-5,7-dimethoxy-1,2,3,4-tetrahydrocarbazole-4-carboxylic acid hydrazide; 9-benzyl-5,7-dimethoxy-1,2,3,4-tetrahydrocarbazole-4-carboxamide; [9-benzyl-4-carbamoyl-7-methoxy-1,2,3,4-tetrahydrocarbazol-5-yl]oxyacetic acid sodium salt; 4-[9-benzyl-4-carbamoyl-7-(2-cyanoethyl)-1,2,3,4-tetrahydrocarbazol-6-yl]oxybutyric acid; [9-benzyl-4-carbamoyl-7-methoxycarbazol-5-yl]oxyacetic acid; methyl[9-benzyl-4-carbamoyl-7-methoxycarbazol-5-yl]oxyacetic acid; 9-benzyl-7-methoxy-5-cyanomethyloxy-1,2,3,4-tetrahydrocarbazole-4-carboxamide; 9-benzyl-7-methoxy-5-(1H-tetrazol-5-yl-methyl)oxy)-1,2,3,4-tetrahydrocarbazole-4-carboxamide; [9-benzyl-4-carbamoyl-8-methyl-1,2,3,4-tetrahydrocarbazole-5-yl]oxyacetic acid; [9-benzyl-4-carbamoyl-8-methyl-carbazole-5-yl]oxyacetic acid; [9-benzyl-4-carbamoyl-1,2,3,4-tetrahydrocarbazol-5-yl]oxyacetic acid; and [9-benzyl-4-carbamoyl-carbazole-5-yl]oxyacetic acid or a pharmaceutically acceptable salt, racemate, solvate, tautomer, optical isomer or prodrug derivative thereof.

3. A method for treating a mammal, including a human, afflicted with Alzheimer's disease to prevent or diminish the rate of further deterioration; said method comprising administering to said mammal a therapeutically effective amount of a substituted tricyclic sPLA$_2$ inhibitor represented by the formula (III);

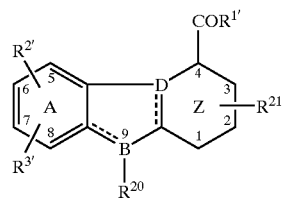

(III)

wherein;

A is phenyl or pyridyl wherein the nitrogen is at the 5-, 6-, 7- or 8-position;

one of B or D is nitrogen and the other is carbon;

Z is cyclohexenyl, phenyl, pyridyl, wherein the nitrogen is at the 1-, 2- or 3-position, or a 6-membered heterocyclic ring having one heteroatom selected from the group consisting of sulfur or oxygen at the 1-, 2- or 3-position, and nitrogen at the 1-, 2-, 3- or 4-position;

==== is a double or single bond;

$R^{20}$ is selected from groups (a), (b) and (c) where;
 (a) is —(C$_5$–C$_{20}$)alkyl, —(C$_5$–C$_{20}$)alkenyl, —(C$_5$–C$_{20}$)alkynyl, carbocyclic radicals, or heterocyclic radicals, or
 (b) is a member of (a) substituted with one or more independently selected non-interfering substituents; or
 (c) is the group —(L)—$R^{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) and carbon, hydrogen, and oxygen only; and where $R^{80}$ is a group selected from (a) or (b);

$R^{21}$ is a non-interfering substituent;

$R^{1'}$ is —NHNH$_2$ or —NH$_2$;

$R^{2'}$ is selected from the group —OH, —O(CH$_2$)$_t$R$^5$ where $R^5$ is CN or phenyl, or —(L$_a$)-(acidic group); wherein —(L$_a$)— is an acid linker having an acid linker length of 1 to 7 and t is 1–5;

$R^{3'}$ is selected from non-interfering substituent, carbocyclic radicals, carbocyclic radicals substituted with non-interfering substituents, heterocyclic radicals, and heterocyclic radicals substituted with non-interfering substituents;

or a pharmaceutically acceptable salt, racemate, solvate, tautomer, optical isomer or prodrug derivative thereof;

provided that when $R^{3'}$ is H, $R^{20}$ is benzyl and m is 1 or 2, $R^{2'}$ cannot be —O(CH$_2$)$_m$H;

and when D is nitrogen, the heteroatom of Z is selected from the group consisting of sulfur or oxygen at the 1-, 2- or 3-position and nitrogen at the 1-, 2-, 3- or 4-position.

4. A method for the prophylactic or therapeutic treatment of a mammal afflicted with Alzheimer's disease, said method comprising administering to said mammal an effective amount of a substituted tricyclic type sPLA2 inhibitor selected from the following:

9-benzyl-5,7-dimethoxy-1,2,3,4-tetrahydrocarbazole-4-carboxylic acid hydrazide;

9-benzyl-5,7-dimethoxy-1,2,3,4-tetrahydrocarbazole-4-carboxamide;

[9-benzyl-4-carbamoyl-7-methoxy-1,2,3,4-tetrahydrocarbazol-5-yl]oxyacetic acid sodium salt;

[9-benzyl-4-carbamoyl-7-methoxycarbazol-5-yl]oxyacetic acid;

methyl[9-benzyl-4-carbamoyl-7-methoxycarbazol-5-yl]oxyacetic acid; methyl[9-benzyl-4-carbamoyl-7-methoxycarbazol-5-yl]oxyacetic acid;

9-benzyl-7-methoxy-5-cyanomethyloxy-1,2,3,4-tetrahydrocarbazole-4-carboxamide;

9-benzyl-7-methoxy-5-(1H-tetrazol-5-yl-methyl)oxy)-1,2,3,4-tetrahydrocarbazole-4-carboxamide;

{9-[(phenyl)methyl]-5-carbamoyl-2-methyl-carbazol-4-yl}oxyacetic acid;

{9-[(3-fluorophenyl)methyl]-5-carbamoyl-2-methylcarbazol-4-yl}oxyacetic acid;

{9-[(3-methylphenyl)methyl]-5-carbamoyl-2-methylcarbazol-4-yl}oxyacetic acid;

{9-[(phenyl)methyl]-5-carbamoyl-2-(4-trifluoromethylphenyl)-carbazol-4-yl}oxyacetic acid;

9-benzyl-5-(2-methanesulfonamido)ethyloxy-7-methoxy-1,2,3,4-tetrahydrocarbazole-4-carboxamide;

9-benzyl-4-(2-methanesulfonamido)ethyloxy-2-methoxycarbazole-5-carboxamide;

9-benzyl-4-(2-trifluoromethanesulfonamido)ethyloxy-2-methoxycarbazole-5-carboxamide;

9-benzyl-5-methanesulfonamidoylmethyloxy-7-methoxy-1,2,3,4-tetrahydrocarbazole-4-carboxamide;

9-benzyl-4-methanesulfonamidoylmethyloxy-carbazole-5-carboxamide;

[5-carbamoyl-2-pentyl-9-(phenylmethyl)carbazol-4-yl]oxyacetic acid;

[5-carbamoyl-2-(1-methylethyl)-9-(phenylmethyl)carbazol-4-yl]oxyacetic acid;

[5-carbamoyl-9-(phenylmethyl)-2-[(tri(-1-methylethyl)silyl)oxymethyl]carbazol-4-yl]oxyacetic acid;

[5-carbamoyl-2-phenyl-9-(phenylmethyl)carbazol-4-yl]oxyacetic acid;

[5-carbamoyl-2-(4-chlorophenyl)-9-(phenylmethyl)carbazol-4-yl]oxyacetic acid;

[5-carbamoyl-2-(2-furyl)-9-(phenylmethyl)carbazol-4-yl]oxyacetic acid;

[5-carbamoyl-9-(phenylmethyl)-2-[(tri(-1-methylethyl)silyl)oxymethyl]carbazol-4-yl]oxyacetic acid, lithium salt;

{9-[(phenyl)methyl]-5-carbamoylcarbazol-4-yl}oxyacetic acid;

{9-[(3-fluorophenyl)methyl]-5-carbamoylcarbazol-4-yl}oxyacetic acid;

{9-[(3-phenoxyphenyl)methyl]-5-carbamoylcarbazol-4-yl}oxyacetic acid;

{9-[(2-Fluorophenyl)methyl]-5-carbamoylcarbazol-4-yl}oxyacetic acid;

{9-[(2-trifluoromethylphenyl)methyl]-5-carbamoylcarbazol-4-yl}oxyacetic acid;

{9-[(2-benzylphenyl)methyl]-5-carbamoylcarbazol-4-yl}oxyacetic acid;

{9-[(3-trifluoromethylphenyl)methyl]-5-carbamoylcarbazol-4-yl}oxyacetic acid;

{9-[(1-naphthyl)methyl]-5-carbamoylcarbazol-4-yl}oxyacetic acid;

{9-[(2-cyanophenyl)methyl]-5-carbamoylcarbazol-4-yl}oxyacetic acid;

{9-[(3-cyanophenyl)methyl]-5-carbamoylcarbazol-4-yl}oxyacetic acid;

{9-[(2-methylphenyl)methyl]-5-carbamoylcarbazol-4-yl}oxyacetic acid;

{9-[(3-methylphenyl)methyl]-5-carbamoylcarbazol-4-yl}oxyacetic acid;

{9-[(3,5-dimethylphenyl)methyl]-5-carbamoylcarbazol-4-yl}oxyacetic acid;

{9-[(3-iodophenyl)methyl]-5-carbamoylcarbazol-4-yl}oxyacetic acid;

{9-[(2-Chlorophenyl)methyl]-5-carbamoylcarbazol-4-yl}oxyacetic acid;

{9-[(2,3-difluorophenyl)methyl]-5-carbamoylcarbazol-4-yl}oxyacetic acid;

{9-[(2,6-difluorophenyl)methyl]-5-carbamoylcarbazol-4-yl}oxyacetic acid;

{9-[(2,6-dichlorophenyl)methyl]-5-carbamoylcarbazol-4-yl}oxyacetic acid;

{9-[(3-trifluoromethoxyphenyl)methyl]-5-carbamoylcarbazol-4-yl}oxyacetic acid;

{9-[(2-biphenyl)methyl]-5-carbamoylcarbazol-4-yl}oxyacetic acid;

{9-[(2-Biphenyl)methyl]-5-carbamoylcarbazol-4-yl}oxyacetic acid;

{9-[(2-Biphenyl)methyl]-5-carbamoylcarbazol-4-yl}oxyacetic acid;

[9-Benzyl-4-carbamoyl-1,2,3,4-tetrahydrocarbaole-5-yl]oxyacetic acid;

{9-[(2-Pyridyl)methyl]-5-carbamoylcarbazol-4-yl}oxyacetic acid;

{9-[(3-Pyridyl)methyl]-5-carbamoylcarbazol-4-yl}oxyacetic acid;

[9-benzyl-4-carbamoyl-8-methyl-1,2,3,4-tetrahydrocarbazol-5-yl]oxyacetic acid;

[9-benzyl-5-carbamoyl-1-methylcarbazol-4-yl]oxyacetic acid;

[9-benzyl-4-carbamoyl-8-fluoro-1,2,3,4-tetrahydrocarbazol-5-yl]oxyacetic acid;

[9-benzyl-5-carbamoyl-1-fluorocarbazol-4-yl]oxyacetic acid;

[9-benzyl-4-carbamoyl-8-chloro-1,2,3,4-tetrahydrocarbazol-5-yl]oxyacetic acid;

[9-benzyl-5-carbamoyl-1-chlorocarbazol-4-yl]oxyacetic acid;

[9-[(Cyclohexyl)methyl]-5-carbamoylcarbazol-4-yl]oxyacetic acid;

[9-[(Cyclopentyl)methyl]-5-carbamoylcarbazol-4-yl]oxyacetic acid;

5-carbamoyl-9-(phenylmethyl)-2-[[(propen-3-yl)oxy]methyl]carbazol-4-yl]oxyacetic acid;

[5-carbamoyl-9-(phenylmethyl)-2[(propyloxy)methyl]carbazol-4-yl]oxyacetic acid;

9-benzyl-7-methoxy-5-((carboxamidomethyl)oxy)-1,2,3,4-tetrahydrocarbazole-4-carboxamide;

9-benzyl-7-methoxy-5-cyanomethyloxy-carbazole-4-carboxamide;

9-benzyl-7-methoxy-5-((1H-tetrazol-5-yl-methyl)oxy)-carbazole-4-carboxamide;

9-benzyl-7-methoxy-5-((carboxamidomethyl)oxy)-carbazole-4-carboxamide; and

[9-Benzyl-4-carbamoyl-1,2,3,4-tetrahydrocarbaole-5-yl]oxyacetic acid or a pharmaceutically acceptable racemate, solvate, tautomer, optical isomer, prodrug derivative or salt, thereof.

5. The method as in any one of claims 1 or 2 or 3 or 4 wherein the administration is intravenous.

6. The method as in any one of claims 1 or 2 or 3 or 4 wherein the administration is oral.

7. The method as in any one of claims 1 or 2 or 3 or 4 wherein treatment is of a human and the sPLA$_2$ inhibitor is administered in an effective amount to achieve a human blood level inhibitor concentration of from 250 to 600 nanograms/ml.

8. The method as in any one of claims 1 or 2 or 3 or 4 wherein sPLA$_2$ inhibitor is administered in an effective amount of from 1 mg/kg/day to 5 mg/kg/day.

9. The method as in any one of claims 1 or 2 or 3 or 4 wherein the sPLA$_2$ inhibitor is in the form of a pharmaceutical formulation comprising the compound and a suitable carrier or excipient therefor.

* * * * *